United States Patent [19]
Chamow et al.

[11] Patent Number: 5,849,689
[45] Date of Patent: Dec. 15, 1998

[54] METHOD OF EXTENDING THE PLASMA HALF-LIFE OF DELETION VARIANTS OF HEPATOCYTE GROWTH FACTOR

[75] Inventors: Steven Chamow, San Mateo; Nishit Modi, San Bruno; Ralph Schwall, Pacifica; Thomas Zioncheck, Montara, all of Calif.

[73] Assignee: Genentech, Inc., South San Francisco, Calif.

[21] Appl. No.: 466,326

[22] Filed: Jun. 6, 1995

Related U.S. Application Data

[63] Continuation-in-part of Ser. No. 254,390, Jun. 6, 1994, Pat. No. 5,464,815, which is a continuation-in-part of Ser. No. 118,162, Sep. 8, 1993, abandoned.

[51] Int. Cl.$^6$ .................................................... A61K 38/18
[52] U.S. Cl. .................................... 514/8; 514/12; 514/21
[58] Field of Search ................................ 424/85.1, 85.2; 435/29, 70.3, 70.4; 436/86, 87; 530/412, 413, 423; 517/8, 12, 21

[56] References Cited

U.S. PATENT DOCUMENTS

| | | | |
|---|---|---|---|
| 4,844,895 | 7/1989 | Thorbecke et al. | 424/85.1 |
| 4,889,808 | 12/1989 | Rappaport | 435/240.1 |
| 5,057,494 | 10/1991 | Sheffield | 514/21 |
| 5,110,604 | 5/1992 | Chu et al. | 424/85.2 |
| 5,130,143 | 7/1992 | Strickland et al. | 435/226 |
| 5,175,147 | 12/1992 | Folkman | 514/12 |
| 5,227,158 | 7/1993 | Jardieu | 514/12 |
| 5,234,908 | 8/1993 | Szabo et al. | 514/12 |
| 5,262,298 | 11/1993 | Shipley | 435/6 |
| 5,288,704 | 2/1994 | Ungheri et al. | 514/12 |
| 5,314,872 | 5/1994 | Kato et al. | 514/12 |
| 5,316,921 | 5/1994 | Godowski et al. | 530/399 |
| 5,318,890 | 6/1994 | Rosen et al. | 530/387.3 |
| 5,328,837 | 7/1994 | Godowski et al. | 530/399 |
| 5,389,520 | 2/1995 | Tedder et al. | 435/240.2 |
| 5,571,509 | 11/1996 | Comoglio et al. | 435/194 |

FOREIGN PATENT DOCUMENTS

| | | |
|---|---|---|
| 2070263 | 12/1992 | Canada . |
| 251806 | 1/1988 | European Pat. Off. . |
| 510270 | 10/1992 | European Pat. Off. . |
| 517182 | 12/1992 | European Pat. Off. . |
| 6145065 | 5/1994 | Japan . |
| WO 90/03797 | 4/1990 | WIPO . |
| WO 93/09790 | 5/1993 | WIPO . |

OTHER PUBLICATIONS

Barber et al., "Characterization of a chondroitin 4 –sulfate proteglycan carrier for heparin neutralizing activity (platelet factor 4 ) released from human blood platelets" *Biochimica et Biophysica Acta* 286:312–329 (1972).

Barzu et al., "Heparin–Derived Oligosaccharides: Affinity for Acidic Fibroblast Growth Factor and Effect on Its Growth–Promoting Activity for Human Endothelial Cells" *J. Cell Phys.* 140:538–548 (1989).

Burgess and Maciag, "The Heparin Binding (Fibroblast) Growth Factor Family of Proteins" *Annu. Rev. Biochem.* 58:576–606 (1989).

Gitay–Goren et al., "The Binding of Vascular Endothelial Growth Factor to Its Receptors Is Dependent on Cell Surface–associated Heparin–like Molecules" *Journal of Biological Chemistry* 267:6093–6098 (1992).

(List continued on next page.)

*Primary Examiner*—Jeffrey E. Russel
*Attorney, Agent, or Firm*—Merchant, Gould, Smith, Edell, Welter & Schmidt, P.A.

[57] ABSTRACT

The invention provides a method for extending the plasma half-life of heparin-binding proteins by coadministering such proteins with a therapeutically acceptable compound capable of inhibiting their binding to a low affinity heparin-like binding site on the surface of the cells. In one embodiment of the invention, the heparin-binding protein is a growth factor. The binding inhibitory compound can, for example, be a purified native heparin preparation, a heparin fragment, or another polyanionic compound, such as dextran sulfate, heparan sulfate, pentosan sulfate, or hyaluronate.

23 Claims, 10 Drawing Sheets

OTHER PUBLICATIONS

Handin et al., "Purification and Binding Properties of Human Platelet Factor Four" *Journal of Biological Chemistry* 251:4273–4282 (1976).

Ishihara et al., "Preparation of Affinity–fractionated, Heparin–derived Oligosaccharides and Their Effects on Selected Biological Activities Mediated by Basic Fibroblast Growth Factor" *Journal of Biological Chemistry* 268:4675–4683 (1993).

Kim et al., "Kinetic Analysis of In Vivo Receptor–Dependent Binding of Human Epidermal Growth Factor by Rat Tissues" *J. Pharm. Sci.* 77:200–207 (1988).

Klagsbrun, M., "The Fibroblast Growth Factor Family: Structural and Biological Properties" *Prog. Growth Factor Research* 1:207–235 (1989).

Kobayashi et al., "Hepatocyte Growth Factor Elevates the Activity Levels of Glycolipid Sulfotransferases in Renal Cell Carcinoma Cells" *European Journal of Biochemistry* 219:407–413 (1994).

Kobayashi et al., "Hepatocyte Growth Factor Specifically Binds to Sulfoglycolipids" *Journal of Biological Chemistry* 269(13):9817–9821 (1994).

Liu et al., "Importance of the Liver in Plasma Clearance of Hepatocyte Growth Factor in Rats" *Am. J. Physiol.* (Gastrointest. Liver Physiol. 26) 263:G642–G649 (1992).

Loscalzo et al., "The Interaction of Platelet Factor Four and Glycosaminglycans" *Archives of Biochemistry & Biophysics* 240:446–455 (1985).

Matsumoto et al., "Heparin as an Inducer of Hepatocyte Growth Factor" *J. Biochem.* 114:820–826 (1993).

Mizuno et al., "Hairpin loop and second kringle domain are essential sites for heparin binding and biological activity of hepatocyte growth factor" *Journal of Biological Chemistry* 269(2):1131–1136 (1994).

Moscatelli, David, "Metabolism of Receptor–bound and Matrix–bound Basic Fibroblast Growth Factor by Bovine Capillary Endothelial Cells" *Journal of Cell Biology* 107:753–759 (1988).

Mueller et al., "Stabilization by Heparin of Acidic Fibroblast Growth Factor Mitogenicity for Human Endothelial Cells in Vitro" *J. Cell. Phys.* 140:439–448 (1989).

Naka et al., "Heparin modulates the receptor–binding and mitogenic activity of hepatocyte growth factor on hepatocytes" *Exp. Cell Res.* 209:317–324 (1993).

Norgard–Sumnicht et al., "Calcium–Dependent Heparin–Like Ligands for L–Selectin in Nonlymphoid Endothelial Cells" *Science* 261:480–483 (1993).

Poschmann et al., "Exchange Transfusion with Heparinished Fresh Blood in Necrotising Enterocolitis" *Lancet* pp. 824–825 (1979).

Saksela et al., "Endothelial Cell–derived Heparan Sulfate Binds Basic Fibroblast Growth Factor and Protects It From Proteolytic Degradation" *J. Cell. Phys.* 107:743–751 (1988).

Soker et al., "Vascular Endothelial Growth Factor Is Inactivated by Binding to alpha 2–macroglobulin and the binding is inhibited by heparin" *Journal of Biological Chemistry* 268(11):7685–7691 (1993).

Sugiyama et al., "Receptor–Mediated Disposition of Polypeptides: Kinetic Analysis of the Transport of Epidermal Growth Factor as a Model Peptide Using in Vitro Isolated Perfused Organs and in Vivo System" *J. Controlled Release* 13:157–174 (1990).

Sugiyama et al., "Receptor–Mediated Hepatic Clearance of Peptide Hormones" *Topics in Pharmaceutical Sciences* pp. 429–443 (1989).

Sugiyama et al., "Receptor–Mediated Transport of Peptide Hormones and its Importance in the Overall Hormone Dispositionin the Body" *Pharm. Res.* 6:192–202 (1989).

Talpas et al., "H–NMR Studies of Bovine Platelet Factor 4: Histidine Assignments and Interactions with Heparin" *Biochimica et Biophysica Acta* 1078:208–218 (1991).

Thomas et al., "Pure Brain–Derived Acidic Fibroblast Growth Factor is a Potent Angiogenic Vascular Endothelial Cell Mitogen with Sequence Homology to Interleukin 1" *Proc. Natl. Acad. Sci.* 82:6009–6413 (1985).

Tyrrell et al., "Structure and Biological Activities of a Heparin–derived Hexasaccharide with High Affinity for Basic Fibroblast Growth Factor" *Journal of Biological Chemistry* 268:4684–4689 (1993).

Webb et al., "Binding to Heparan Sulfate or Heparin Enhances Neutrophil Responses to Interleukin 8" *Proc. Natl. Acad. Sci.* 90:7158–7162 (1993).

Yayon et al., "Cell Surface, Heparin–like Molecules are Required for Binding of Basic Fibroblast Growth Factor to its High Affinity Receptor" *Cell* 64:841–848 (1991).

Zucker et al., "Immunoregulatory Activity of Peptides Related to Platelet Factor 4" *Proc. Natl. Acad. Sci.* 86:7571–7574 (1989).

Lokker et al. Generation and Characterization of a Competitive . . . J. Biol. Chem. 15 Aug. 1993, vol. 268, No. 23 pp. 17145–17150.

|  | HGF | HGF + heparin |
| --- | --- | --- |
| CL (mL/min/kg) | 20.7 ± 3.5 | 3.6 ± 0.7 |
| $V_1$(mL/kg) | 120 ± 25 | 67.7 ± 21 |
| $V_{ss}$(mL/kg) | 2050 ± 662 | 148 ± 82 |
| MRT(hr) | 1.7 ± 0.8 | 0.7 ± 0.3 |
| $t_{1/2\alpha}$(min) | 1.6 ± 0.3 | |
| $t_{1/2\beta}$(min) | 16.0 ± 9.8 | 12.3 ± 1.8 |
| $t_{1/2\gamma}$(hr) | 2.4 ± 0.9 | 4.1 ± 1.4 |

METHOD OF EXTENDING THE PLASMA HALF-LIFE OF DELETION VARIANTS OF HEPATOCYTE GROWTH FACTOR

The present application is a continuation-in-part application of application Ser. No. 08/254,390 filed on Jun. 6, 1994, now U.S. Pat. No. 5,464,815, which is a continuation-in-part application of application Ser. No. 08/118,162 filed Sep. 8, 1993, now abandoned, incorporated herein by reference.

FIELD OF THE INVENTION

The present invention concerns improvements in the purification, testing and therapeutic use of heparin-binding proteins, based upon the inhibition of the interaction between such proteins and naturally occurring heparin-like substances. More specifically, the invention relates to improved methods and compositions for the administration of heparin-binding proteins. The invention further relates to improved methods for the purification and for testing the biological activity of heparin-binding proteins.

BACKGROUND OF THE INVENTION

It is known that a large variety of naturally occurring, biologically active polypeptides bind heparin. Such heparin-binding polypeptides include cytokines (also termed chemokines), such as platelet factor 4 and IL-8 (Barber et al., *Biochim. Biophys. Acta* 286, 312–329 (1972); Handin et al., *J. Biol. Chem.* 251, 4273–422 (1976); Loscalzo et al., *Arch. Biochem. Biophys.* 240, 446–455 (1985); Zucker et al., *Proc. Natl. Acad. Sci. USA* 86, 7571–7574 (1989); Talpas et al., *Biochim. Biophys. Acta* 1078, 208–218 (1991); Webb et al., *Proc. Natl. Acad. Sci. USA* 90, 7158–7162 (1993)); heparin-binding growth factors (Burgess and Maciag, *Annu. Rev. Biochem.* 58, 576–606 (1989); Klagsbrun, *Prog. Growth Factor Res.* 1, 207–235 (1989)), such as epidermal growth factor (EGF); platelet-derived growth factor (PDGF); basic fibroblast growth factor (bFGF); acidic fibroblast growth factor (aFGF); vascular endothelial growth factor (VEGF); and hepatocyte growth factor (HGF) (for the latter see also Liu et al., *Am. J. Physiol.* 263, (*Gastrointest. Liver Physiol.* 26, G642–G649 (1992)); and selectins, such as L-selectin, E-selectin and P-selectin (Norgard-Sumnicht et al., *Science* 261, 480–483 (1993)).

The preparation of homogeneously sized, heparin-derived oligosaccharides prepared from heparin has been reported, and heparin-derived hexa- and octasaccharides were described to be able to inhibit the interaction between cell surface heparan proteoglycan and bFGF (Ishihara et al., *J. Biol. Chem.* 268, 4675–4683 (1993)). The structure of a specific heparin-derived hexasaccharide showing high affinity for bFGF was described by Tyrrell et al., *J. Biol. Chem.* 268, 4684–4689 (1993).

The heparin-binding proteins are typically cleared rapidly from the plasma in vivo, and this rapid clearance greatly limits their therapeutic applications. Although the liver and the kidney have been identified as the major clearance organs for a number of heparin-binding proteins (see, e.g. Kim et al., *J. Pharm. Sci.* 77, 200–207 (1988); Sugiyama et al., *Pharm. Res.* 6, 194–204 (1989), Sugiyama et al., *J. Controlled Release* 13, 157–174 (1990) and Sugiyama et al., Receptor Mediated Hepatic Clearance of Peptide Hormones, In: Topics in Pharmaceutical Sciences 1989, Breimer et al., eds., Elsevier, New York, 1989, p. 429–443), little is known about the mechanism of their rapid removal from the circulation. In a recent publication (Liu et al., supra) it was proposed that there are at least two different kinds of binding sites for HGF on the surface of hepatic cells: a heparin-washable binding site with lower affinity and a heparin-resistant, acid-washable binding site with higher affinity, and that the low-affinity binding site appears to play a role in the internalization of HGF. The binding of other heparin-binding proteins to their respective cell surface receptors was described to be dependent upon heparin-like molecules (see, e.g. Gitay-Goren et al., *J. Biol. Chem.* 267, 6093–6098 (1992) for VEGF), and it was shown that the addition of exogenous heparin is able to potentiate the binding of certain heparin-binding proteins to their receptors.

It would be desirable to increase the plasma half-life and/or decrease the plasma clearance of heparin-binding proteins.

It would further be desirable to improve the therapeutic potency of heparin-binding proteins.

It would also be desirable to improve the bioavailability of such polypeptides when they are not directly administered into the blood stream.

It would additionally be desirable to prevent the inactivation of heparin-binding polypeptides by other binding proteins in blood.

It would further be desirable to enhance the sensitivity of assays for the detection of heparin-binding proteins.

It would be also desirable to enhance the purification of heparin-binding proteins from cell cultures.

Accordingly, it is an object of the present invention to provide a method for extending the plasma half-life of heparin-binding proteins.

It is another object of the invention to improve the therapeutic potency of heparin-binding proteins.

It is a further object, to improve the bioavailability of heparin-binding proteins.

It is a still further object to provide methods for preventing the inactivation of heparin-binding proteins by other blood proteins.

It is yet another object to provide new and improved pharmaceutical compositions of heparin-binding proteins.

It is an additional object to enhance the sensitivity of assays for the detection of heparin-binding proteins.

It is a still further object to facilitate the purification of heparin-binding proteins.

It is another object of the present invention to provide methods for the intraperitoneal or subcutaneous administration of heparin-binding proteins.

SUMMARY OF THE INVENTION

The present invention is based on the finding that the in vivo half-life of heparin-binding growth factors, such as HGF, in the plasma can be significantly extended by coadministration with a polyanionic molecule, such as heparin or heparin-derived oligosaccharides. It has further been found that the coadministration of polyanionic molecules increases the amount of heparin-binding proteins entering the plasma after intraperitoneal or subcutaneous administration. Although it is believed that the effect of polyanionic molecules on the bioavailability of heparin-binding proteins is due to their ability to block the binding of heparin-binding proteins to extracellular matrix glycosylaminoglycans, the invention is not limited by this or any other theory in any way. The invention is additionally based on the finding that the presence of polyanionic molecules, and specifically heparin and heparin-like oligosaccharides potentiates the biological activity of heparin-binding proteins (HGF, IL-8) and/or enhances their binding to their respective native receptors (VEGF).

In one aspect, the invention concerns a method for extending the plasma half-life of a heparin-binding protein comprising coadministering such protein with a therapeutically acceptable compound capable of inhibiting its binding to a low affinity heparin-like binding site on the surface of cells of an organ highly perfused with blood.

In another aspect, the invention concerns a method for improving the therapeutic potency of a heparin-binding protein comprising coadministering with a therapeutically effective amount of the protein a therapeutically acceptable polyanionic compound.

In a further aspect, the invention concerns a method of improving the bioavailability of a heparin-binding protein comprising coadministering the protein with a therapeutically acceptable compound capable of inhibiting its interaction with heparin-like substances in the extracellular matrix.

In a still further aspect, the invention concerns a method for preventing the inactivation of a heparin-binding protein by a serum protein, which comprises coadministering the heparin-binding protein with a polyanionic compound, such as dextran sulfate, heparin sulfate, heparan sulfate or a functional derivative thereof.

In yet another aspect, the invention concerns a pharmaceutical composition comprising a therapeutically effective amount of a heparin-binding protein in association with a polyanionic compound.

In an additional aspect, the invention concerns a method for enhancing the sensitivity of an assay for the detection of a heparin-binding protein in a test sample, which method comprises the addition of a polyanionic compound to the test sample.

In a further aspect, the invention concerns a method for the purification of a heparin-binding protein from a cell culture comprising supplementing the cell culture with a compound capable of inhibiting the binding of the heparin-binding protein to heparin-like substances therein.

In a further aspect, the invention concerns a method for the induction of hepatocyte growth by administering to a patient in need of such treatment a therapeutically effective amount of hepatocyte growth factor (HGF) in combination with a polyanionic compound, preferably a dextran or dextran sulfate.

In a still further aspect, the invention concerns a method for modulating biological activity of a heparin-binding protein such as HGF and particularly, a variant of HGF referred to as NK1.

DETAILED DESCRIPTION OF THE INVENTION

I. Definitions

Figure 1:
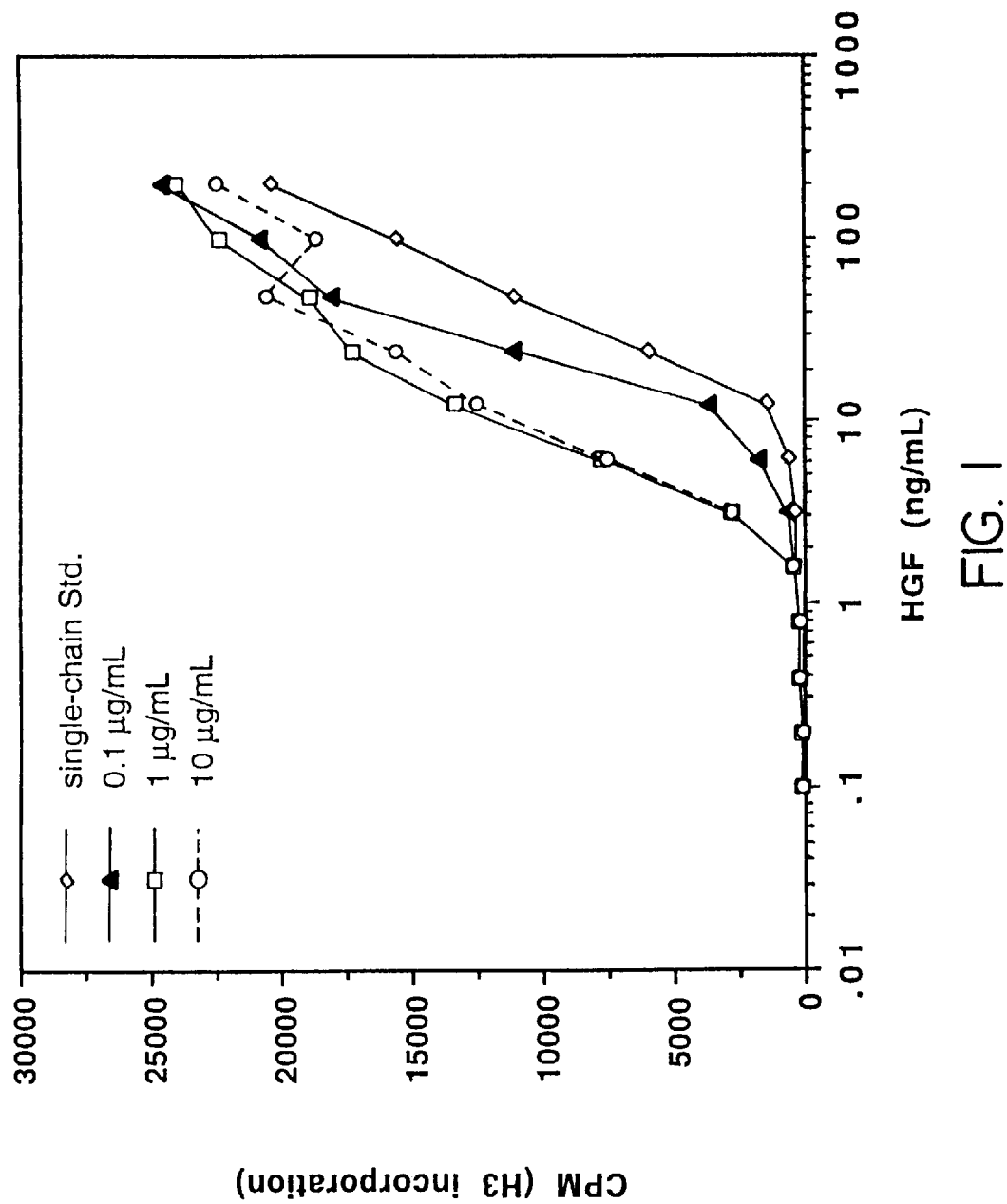
FIG. 1 shows the effect of heparin on the biological activity of HGF.
Figure 2:
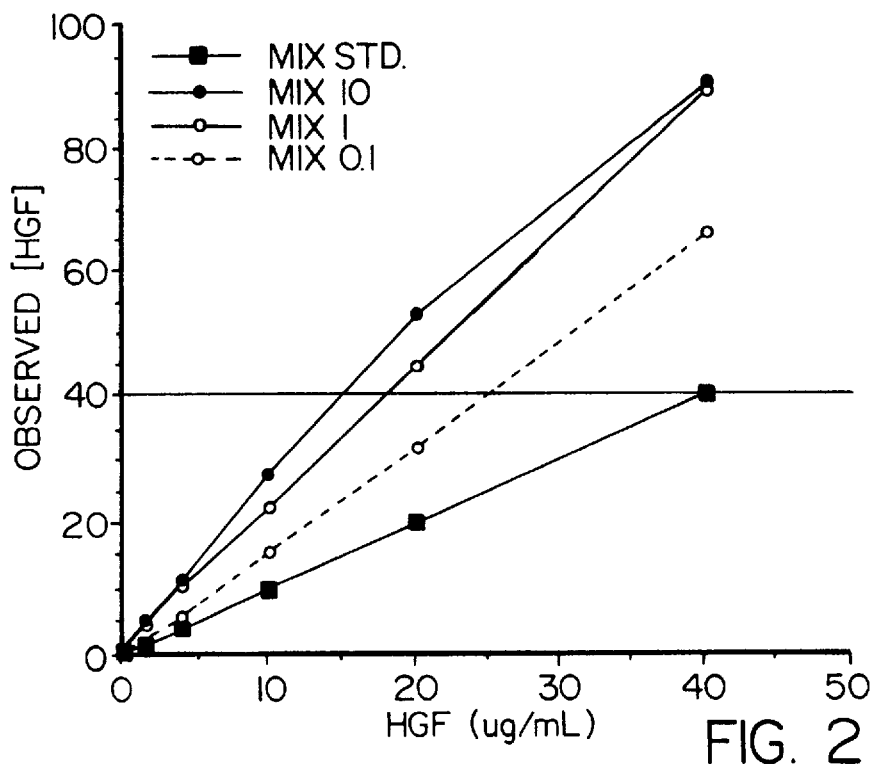
FIG. 2 shows the effect of heparin on the detection of HGF in an ELISA.

"Heparin" (also referred to a heparinic acid) is a heterogeneous group of highly sulfated, straight-chain anionic mucopolysaccharides, called glycosaminoglycans. Although others may be present, the main sugars in heparin are: α-L-iduronic acid 2-sulfate, 2-deoxy-2-sulfamino-α-glucose 6-sulfate, β-D-glucuronic acid, 2-acetamido-2-deoxy-α-D-glucose, and L-iduronic acid. These and optionally other sugars are joined by glycosidic linkages, forming polymers of varying sizes. Due to the presence of its covalently linked sulfate and carboxylic acid groups, heparin is strongly acidic. The molecular weight of heparin varies from about 6,000 to about 20,000 Da depending on the source and the method of determination. Native heparin is a constituent of various tissues, especially liver and lung, and mast cells in several mammalian species. Heparin and heparin salts (heparin sodium) are commercially available and are primarily used as anticoagulants in various clinical situations.

The term "heparin-binding protein" as used herein refers to a polypeptide capable of binding heparin (as hereinabove defined). The definition includes the mature, pre, pre-pro, and pro forms of native heparin-binding proteins, if any, purified from natural source, chemically synthesized or recombinantly produced, their functional derivatives and inhibitors. Typical examples of heparin-binding proteins are growth factors, including but not limited to epidermal growth factor (EGF), platelet derived growth factor (PDGF), basic fibroblast growth factor (bFGF), acidic fibroblast growth factor (aFGF), vascular endothelial growth factor (VEGF), hepatocyte growth factor (HGF) (also known as scatter factor, SF), NGF, IL-8, etc.

A "functional derivative" of a native heparin-binding protein is a compound that retains at least one qualitative biological activity of the corresponding native protein and has the ability to bind heparin. Functional derivatives include, but are not limited to, fragments of native heparin-binding proteins from any animal species, and derivatives of the native proteins and fragments thereof, wherein the term "derivative" is used to define amino acid sequence and glycosylation variants, and covalent modifications of a native protein, whereas the term "variant" refers to amino acid sequence and glycosylation variants within this definition. An "inhibitor" of a native heparin-binding protein is a compound that inhibits at least one biological activity of the corresponding native protein and has the ability to bind heparin.

The term "amino acid sequence variant" refers to molecules with some differences in their amino acid sequences as compared to a native sequence heparin-binding protein or a fragment thereof. Ordinarily, the amino acid sequence variants will possess at least about 70%, preferably at least about 80%, more preferably at least about 90%, most preferably at least about 95% homology with a native heparin-binding protein, or with a fragment thereof which retains at least the regions required for heparin binding and for binding to the receptor(s) mediating the biological activity of the protein. Such amino acid sequence variants are preferably encoded by DNA capable, under stringent conditions, of hybridizing to the complement of DNA encoding the corresponding native heparin-binding protein or a fragment thereof. The amino acid sequence variants possess substitutions, deletions, and/or insertions at certain positions within the amino acid sequence of a native heparin-binding protein.

"Homology" is defined as the percentage of residues in the candidate amino acid sequence that are identical with the residues in the amino acid sequence of a native heparin-binding protein or a fragment thereof, after aligning the sequences and introducing gaps, if necessary, to achieve the maximum percent homology. Methods and computer programs for the alignment are well known in the art.

"Stringent conditions" are overnight incubation at 37° C. in a solution comprising: 40% formamide, 5× SSC (150 mM NaCl, 15 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 1× SSC at about 50° C.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native ligand sequence. Immediately adjacent to an amino acid means connected to either the α-carboxy or α-amino functional group of the amino acid.

Deletional variants are those with one or more amino acids in the native ligand amino acid sequence removed. Ordinarily, deletional variants will have one or two amino acids deleted in a particular region of the molecule.

The term "glycosylation variant" is used to refer to a heparin-binding protein molecule having a glycosylation profile different from that of a corresponding native protein. Glycosylation of polypeptides is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation. Any difference in the location and/or nature of the carbohydrate moieties present in a glycosylation variant or fragment as compared to its native counterpart is within the scope herein.

The glycosylation pattern of native polypeptides can be determined by well known techniques of analytical chemistry, including HPAE chromatography [Hardy, M. R. et al., Anal. Biochem. 170, 54–62 (1988)], methylation analysis to determine glycosyl-linkage composition [Lindberg, B., Meth. Enzymol. 28. 178–195 (1972); Waeghe, T. J. et al., Carbohydr. Res. 123, 281–304 (1983)], NMR spectroscopy, mass spectrometry, etc.

"Covalent derivatives" include modifications of a native heparin-binding protein or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected side-chains or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the heparin-binding protein molecules as defined in the present invention. Other post-translational modifications include hydroxylation of proline and lysine, phosphorylation of hydroxyl groups of seryl, threonyl, or tyrosyl residues, methylation of the α-amino groups of lysine, arginine, and histidine side chains [T. E. Creighton, Proteins: Structure and Molecular Properties, W. H. Freeman & Co., San Francisco, pp. 79–86 (1983)].

"Biological activity" is defined as either 1) immunological cross-reactivity with at least one epitope of a native heparin-binding protein, or 2) the possession of at least one adhesive, regulatory or effector function qualitatively in common with a native heparin-binding protein.

"HGF" was identified initially as a mitogen for hepatocytes [Michalopoulos et al., Cancer Res.44, 4414–4419 (1984); Russel et al., J. Cell. Physiol. 119, 183–192 (1984) and Nakamura et al., Biochem. Biophys. Res. Comm. 122:1450–1459 (1984)]. Nakamura et al., supra reported the purification of HGF from the serum of partially hepatectomized rats. Subsequently, HGF was purified from rat platelets, and its subunit structure was determined [Nakamura et al., Proc. Natl. Acad. Sci. USA, 83, 6489–6493 (1986); and Nakamura et al., FEBS Letters 224, 311–316 (1987)]. The purification of human HGF (huHGF) from human plasma was first described by Gohda et al., J. Clin. Invest. 81, 414–419 (1988).

Both rat HGF and huHGF have been molecularly cloned, including the cloning and sequencing of a naturally occurring variant lacking 5 amino acids designated "delta5 HGF" [Miyazawa et al., Biochem. Biophys. Res. Comm. 163, 967–973 (1989); Nakamura et al., Nature 342, 440–443 (1989); Seki et al, Biochem. and Biophys. Res. Commun. 172, 321–327 (1990); Tashiro et al., Proc. Natl. Acad. Sci.

USA 87, 3200–3204 (1990); Okajima et al., *Eur. J. Biochem.* 193, 375–381 (1990)].

The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the hHGF cDNA reveals that both the α- and the β-chains are contained in a single open reading frame coding for a pre-pro precursor protein. In the predicted primary structure of mature hHGF, an interchain S—S bridge is formed between Cys 487 of the α-chain and Cys 604 in the β-chain (see Nakamura et al., *Nature*, supra). The N-terminus of the α-chain is preceded by 54 amino acids, starting with a methionine group. This segment includes a characteristic hydrophobic leader (signal) sequence of 31 residues and the prosequence. The α-chain starts at amino acid (aa) 55, and contains four Kringle domains. The Kringle 1 domain extends from about aa 128 to about aa 206, the Kringle 2 domain is between about aa 211 and about aa 288, the Kringle 3 domain is defined as extending from about aa 303 to about aa 383, and the Kringle 4 domain extends from about aa 391 to about aa 464 of the α-chain. It will be understood that the definition of the various Kringle domains is based on their homology with kringle-like domains of other proteins (prothrombin, plasminogen), therefore, the above limits are only approximate. As yet, the function of these Kringles has not been determined. The β-chain of huHGF shows high homology to the catalytic domain of serine proteases (38% homology to the plasminogen serine protease domain). However, two of the three residues which form the catalytic triad of serine proteases are not conserved in huHGF. Therefore, despite its serine protease-like domain, hHGF appears to have no proteolytic activity and the precise role of the β-chain remains unknown. HGF contains four putative asparagine-linked glycosylation sites, which are located at positions 294 and 402 of the β-chain and at positions 566 and 653 of the β-chain, in addition an O-linked oligosaccharide is attached to Thr-445 [Shimizu et al., *Biochem. Biophys. Res. Comm.* 189: 1329–1335 (1992)].

In a portion of cDNA isolated from human leukocytes in-frame deletion of 15 base pairs was observed. Transient expression of the cDNA sequence in COS-1 cells revealed that the encoded HGF molecule (delta5 HGF) lacking 5 amino acids in the Kringle 1 domain was fully functional (Seki et al., supra).

A naturally occurring huHGF variant has recently been identified which corresponds to an alternative spliced form of the huHGF transcript containing the coding sequences for the N-terminal finger and first two kringle domains of mature huHGF [Chan et al., *Science* 254, 1382–1385 (1991); Miyazawa et al., *Eur. J. Biochem.* 197, 15–22 (1991)]. This variant, designated HGF/NK2, has been proposed to be a competitive antagonist of mature huHGF. Another variant, referred to as HGF/NK1, containing the coding sequences for the N-terminal finger and the first kringle domain of mature huHGF has also been proposed to antagonize the proliferative effects of HGF in rat hepatocytes [Lokker et al., *J. Biol. Chem.*, 268:17145–17150 (1993)].

The comparison of the amino acid sequence of rat HGF with that of huHGF revealed that the two sequences are highly conserved and have the same characteristic structural features. The length of the four Kringle domains in rat HGF is exactly the same as in huHGF. Furthermore, the cysteine residues are located in exactly the same positions; an indication of similar three-dimensional structures (Okajima et al., supra; Tashiro et al., supra).

The HGF receptor has been identified as the product of the c-Met proto-oncogene [Bottaro et al., *Science*, 251:802–804 (1991); Naldini et al., *Oncogene*, 6:501–504 (1991); WO 92/13097 published Aug. 6, 1992; WO 93/15754 published Aug. 19, 1993]. The receptor is usually referred to as "c-Met" or "p190$^{MET}$" and typically comprises, in its native form, a 190-kDa heterodimeric (a disulfide-linked 50-kDa α-chain and a 145-kDa β-chain) membrane-spanning tyrosine kinase protein [Park et al., *Proc. Natl. Acad. Sci. USA*, 84:6379–6383 (1987)]. Several truncated forms of the c-Met receptor have also been described [WO 92/20792; Prat et al., *Mol. Cell. Biol.*, 11:5954–5962 (1991)].

Binding by HGF can activate the c-Met kinase and lead to increased proliferation and motility, which can be manifested as dissociation (scattering) of tight clusters in cells such as MDCK. The binding activity of HGF to its receptor is believed to be conveyed by a functional domain located in the N-terminal portion of the HGF molecule, including the first two kringles [Matsumoto et al., *Biochem. Biophys. Res. Commun.*, 181:691–699 (1991); Hartmann et al., *Proc. Natl. Acad. Sci.*, 89:11574–11578 (1992); Lokker et al., *EMBO J.*, 11:2503–2510 (1992); Lokker and Godowski, *J. Biol. Chem.*, 268:17145–117150 (1991)]. The c-Met protein becomes phosphorylated on tyrosine residues of the 145-kDa β-subunit upon HGF binding.

For further information about HGF see: "Hepatocyte Growth Factor—Scatter Factor (HGF-SF) and the C-Met Receptor", I. D. Goldberg and E. M. Rosen eds., Birkhäuser Verlag, 1993.

As used herein, the terms "hepatocyte growth factor", "HGF" and "huHGF" refer to a (human) growth factor capable of specific binding to a receptor of wild-type (human) HGF, which growth factor typically has a structure with six domains (finger, Kringle 1, Kringle 2, Kringle 3, Kringle 4 and serine protease domains), but nonetheless may have fewer domains or may have some of its domains repeated if it still retains its qualitative HGF receptor binding ability. This definition specifically includes the delta5 huHGF as disclosed by Seki et al., supra, and HGF variants having less than four kringle domains, such as HGF/NK1 and HGF/NK2. The terms "hepatocyte growth factor" and "HGF" also include hepatocyte growth factor from any non-human animal species, and in particular rat HGF.

The terms "wild-type human hepatocyte growth factor", "native human hepatocyte growth factor", "wild-type huHGF" and "native huHGF" refer to native sequence human HGF, i.e., that encoded by the cDNA sequence published by Miyazawa, et al. 1989, supra, or Nakamura et al., 1989, supra, including its mature, pre, pre-pro, and pro forms, purified from natural source, chemically synthesized or recombinantly produced. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms as defined for the purpose of the present invention. It will be understood that natural allelic variations exist and can occur among individuals, as demonstrated by one or more amino acid differences in the amino acid sequence of each individual. Amino acid positions in the variant huHGF molecules herein are indicated in accordance with the numbering of Miyazawa et al. 1989, supra.

The biological activity of a native HGF is shared by a functional derivative thereof that has a qualitative mitogenic, motogenic or morphogenic activity exhibited by a native HGF or that possesses an immune epitope that is immunologically cross-reactive with an antibody raised against at least one epitope of the corresponding native HGF. The HGF biological activity may, for example, be determined in an in vitro or in vivo assay of hepatocyte growth promotion. Adult rat hepatocytes in primary culture have been extensively used to search for factors that regulate hepatocyte proliferation. Accordingly, the mitogenic effect of an HGF variant can be conveniently determined in an assay suitable for testing the ability of an HGF molecule to induce DNA synthesis of rat hepatocytes in primary cultures, such as, for example, described in Example 2. Human hepatocytes are also available from whole liver perfusion on organs deemed unacceptable for transplantation, pare-downs of adult livers used for transplantation in children, fetal livers and liver remnants removed at surgery for other indications. Human hepatocytes can be cultured similarly to the methods established for preparing primary cultures of normal rat hepatocytes. Hepatocyte DNA synthesis can, for example, be assayed by measuring incorporation of [$^3$H]thymidine into DNA, with appropriate hydroxyurea controls for replicative synthesis.

The effect of HGF variants on hepatocyte growth can also be tested in vivo in animal models of liver dysfunction and regeneration, such as in rats following partial hepatectomy, or carbon tetrachloride caused hepatic injury, in D-galactosamine induced acute liver failure models, etc. According to a suitable protocol, a liver poison, e.g. α-naphthylisothiocyanate (ANIT) is administered to rats in a predetermined concentration capable of causing reproducible significant elevation of liver enzyme and bilirubin levels. The rats are then treated with the HGF variant to be tested, sacrificed and the liver enzyme and bilirubin levels are determined. The livers are additionally observed for hepatic lesions.

The terms "agonist" and "agonistic" when used herein refer to or describe a molecule which is capable of, directly or indirectly, substantially inducing, promoting or enhancing HGF biological activity or HGF receptor activation.

The terms "antagonist" and "antagonistic" when used herein refer to or describe a molecule which is capable of, directly or indirectly, substantially counteracting, reducing or inhibiting HGF biological activity or HGF receptor activation.

As used herein, "vascular growth factor", or "VEGF", refers to a mammalian growth factor derived originally from bovine pituitary follicular cells having the amino acid sequence disclosed in U.S. Pat. No. 5,332,671, together with functional derivatives thereof having the qualitative biological activity of a corresponding native VEGF, including, but not limited to, the human VEGF amino acid sequence. The biological activity of native VEGF is shared by any functional derivative thereof that is capable of promoting selective growth of vascular endothelial cells but not of bovine corneal endothelial cells, lens epithelial cells, adrenal cortex cells, BHK-21 fibroblasts, or keratinocytes, or that possesses an immune epitope that is immunologically cross-reactive with an antibody raised against at least one epitope of the corresponding native VEGF.

The term "selectin" is used to describe cell adhesion molecules also referred to as LEC-CAMs, the number of which currently stands at three: L-selectin (a.k.a. peripheral lymphone node homing receptor (pnHR), LEC-CAM-1, LAM-1, gp90$^{MEL}$, gp100$^{MEL}$, gp110$^{MEL}$, MEL-14 antigen, Leu-8 antigen, TQ-1 antigen, DREG antigen); E-selectin (LEC-CAM-2, LECAM-2, ELAM-1) and P-selectin (LEC-CAM-3, LECAM-3, GMP-140, PADGEM) (see Belacqua et al., Science 243, 1160 (1989) and Geng et al., Nature 343, 757 (1990)). As used herein, the term "selectin" refers to any of the native-sequence selectins from any (human or non-human) animal species, and to their functional derivatives. The biological activity of a native selectin is shared by any functional derivative thereof that has at least one adhesive, regulatory or effector function qualitatively in common with a corresponding native selectin, or that shows immunological cross-reactivity with at least one epitope of a native selectin.

The terms "half-life" and "plasma half-life" refer to the time by which half of the administered amount of a heparin-binding protein is removed from the blood stream.

The terms "clearance rate" and "clearance" refer to the rate at which a heparin-binding protein is removed from the blood stream.

The expressions "biological potency" and "in vivo biological potency" are used to refer to biological activity per unit dose of a heparin-binding protein.

The term "inhibition" in connection with the binding of two substances to one another is used in the broadest sense and includes the complete blocking of binding just as the reduction of the amount of the substance bound.

The term "therapeutically effective dose" is used to refer to an amount sufficient for the prevention or treatment of a specified physiological condition or symptom. Heparin-binding polypeptides to be administered in accordance with the present invention are known in the art, and so are their therapeutically effective doses. The determination of the effective dose for new functional derivatives may require some routine experimentation, but in all instances, the determination of a therapeutically effective dose is well within the skill in the art.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

II. Preferred Embodiments

Figure 3A:
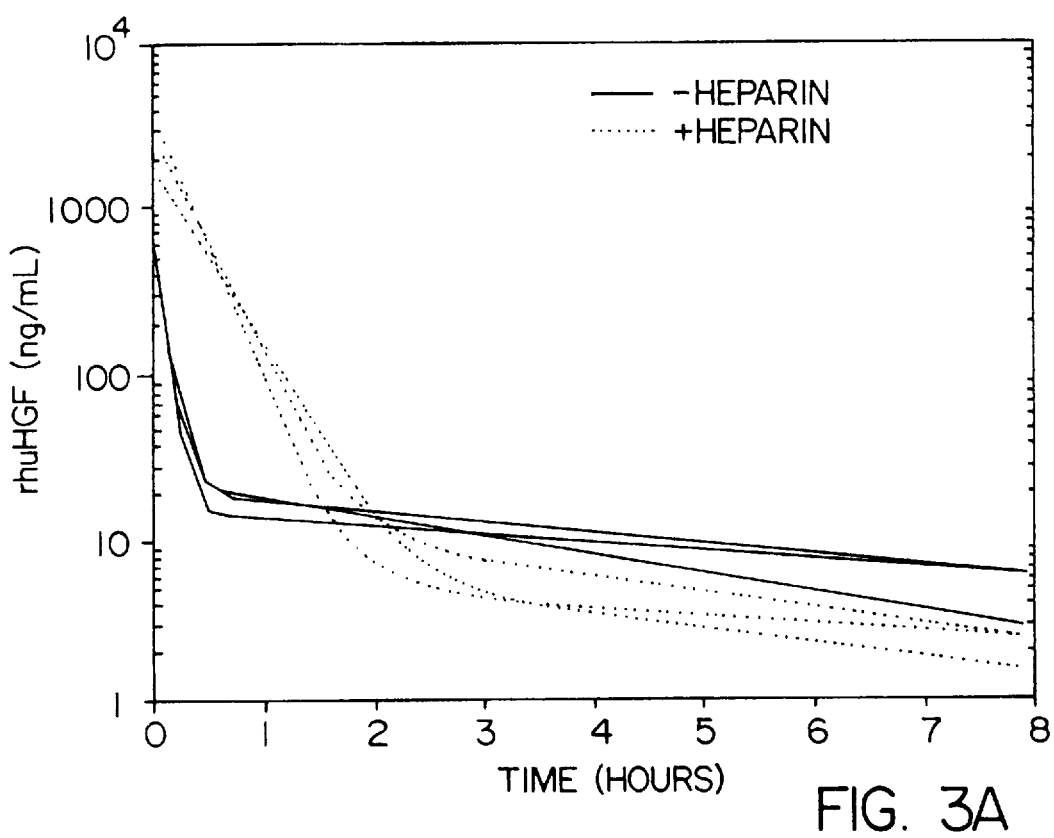
FIGS. 3A–3B shows the effect of heparin on the pharmacokinetics of HGF in vivo.
Figures 3B, 4:
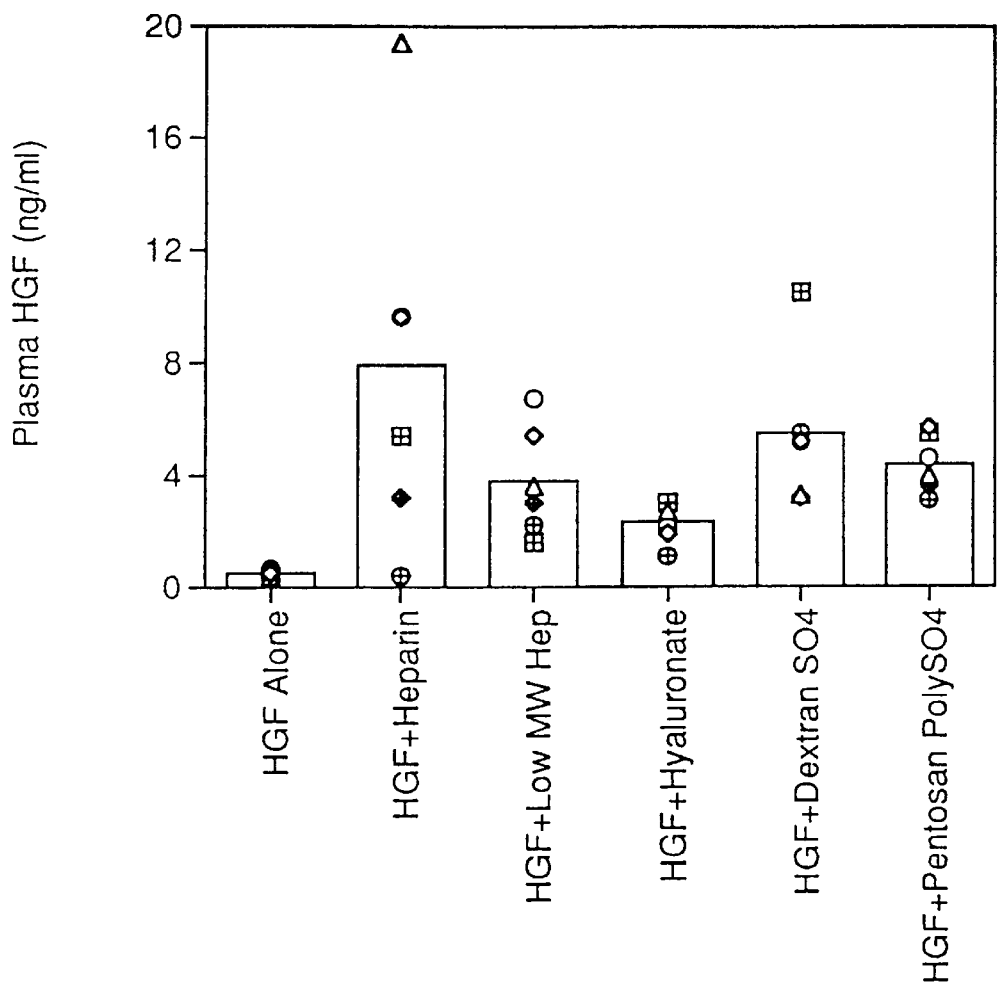
FIG. 4 shows the effect of polyanions on the bioavailability of HGF after subcutaneous administration.
Figure 5A:
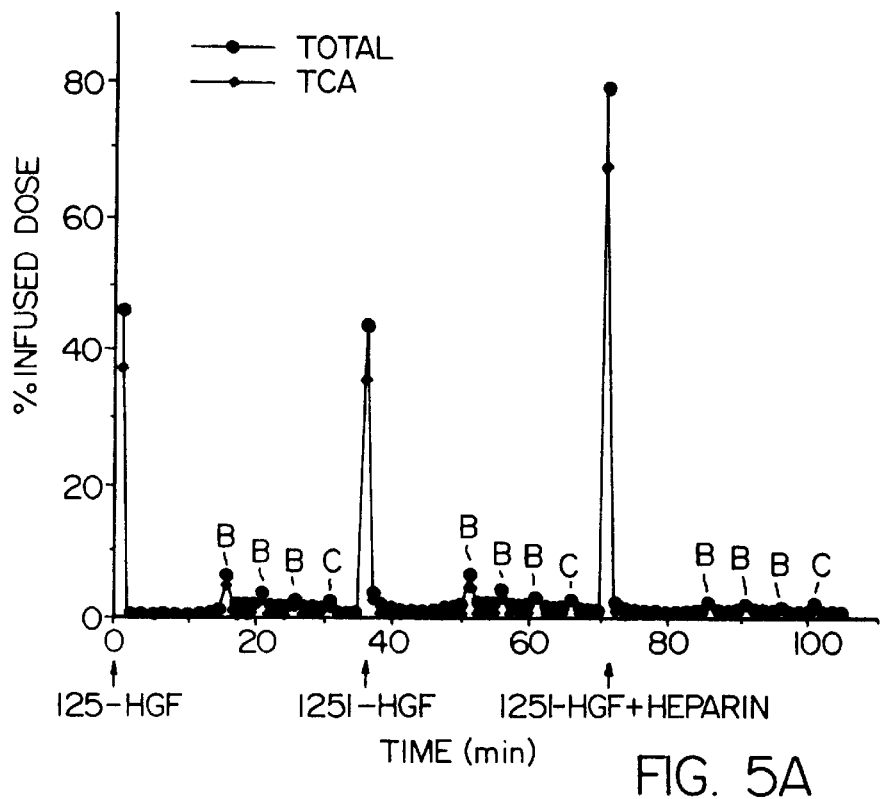
FIGS. 5A–5B show the effect of heparin on the hepatic clearance of [$^{125}$I]HGF.
Figure 5B:
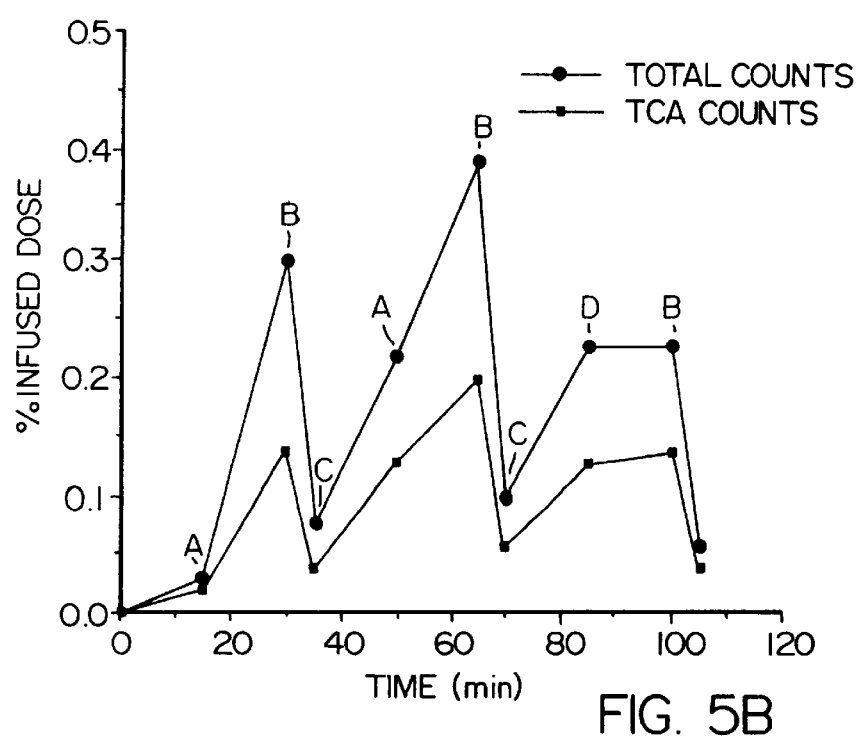

In addition to commercially available purified native heparin preparations (for example from intestinal mucosa), compounds which are capable of inhibiting the binding of a heparin-binding protein to low-affinity heparin-like substances (binding sites) on cell surface or in the extracellular matrix include other polyanionic compounds, such as dextran sulfate, heparan sulfate, pentosan (poly) sulfate, hyaluronate and heparin fragments. Heparin fragments may be obtained from a library of heparin-derived oligosaccharides that have been fractionated by gel-permeation chromatography. The preparation of affinity-fractionated, heparin-derived oligosaccharides was reported by Ishihara et al., J. Biol. Chem. 268, 4675–4683 (1993). These oligosaccharides were prepared from commercial porcine heparin following partial depolymerization with nitrous acid, reduction with sodium borohydride, and fractionation by gel permeation chromatography. The resulting pools of di-, tetra-, hexa-, octa-, and decasaccharides were sequentially applied to an affinity column of human recombinant bFGF covalently attached to Sepharose 4B, and were further fractionated into subpools based on their elution from this column in response to gradients of sodium chloride. This resulted in five pools, designated Hexa-1 to Hexa-5, the structures and biological activities of which were further evaluated. The structure of Hexa-5C and its 500-MHz NMR spectrum are shown in FIG. 4 of Tyrell et al., *J. Biol. Chem.* 268, 4684–4689 (1993). This hexasaccharide has the structure [IdoA(2-OSO$_3$)α1-4GlcNSO$_3$(6-OSO$_3$)α1-4]$_2$IdoA(2-OSO$_3$)α1-4AMan$_R$(6-OSO$_3$). All heparin-derived oligosaccharides discussed above, as well as other heparin-like oligosaccharides are suitable for and can be used in accordance with the present invention. It is preferred, however, to use hexasaccharides and polysaccharides of higher unit size (e.g. hepta-, octa-, nona- and decasaccharides) to practice the present invention. Furthermore, heparin-derived or heparin-like oligosaccharides with a large net negative charge, e.g. due to a high degree of sulfation, are used with advantage. In therapeutic applications, the use of specific heparin fragments has a distinct advantage over that of intact heparin. Heparin is an antithrombotic and may be toxic, especially in higher concentrations. By using smaller heparin fragments, the antithrombin-3 (AT3) binding site of heparin can be effectively engineered out, and thus the fragments are expected to be devoid of antithrombotic properties.

Whereas the use of polyanionic compounds in conjunction with native-sequence heparin-binding proteins is within the scope of the present invention, the methods and compositions herein are equally suitable for the purification, detection and administration of any heparin-binding protein as hereinabove defined, including native heparin-binding proteins, their functional derivatives, and inhibitors of their biological actions.

In a preferred embodiment, the heparin-binding protein is HGF. Optionally, the HGF may be native huHGF, a functional derivative or inhibitor thereof, or variant thereof. HGF variants are, for example, disclosed in U.S. Pat. No. 5,316,921 and U.S. Pat. No. 5,328,837. As it has been shown that the receptor binding domain is contained within the finger and Kringle 1 (K1) regions of the native huHGF molecule, in addition to the heparin-binding site(s), the HGF variants preferably contain a functional finger and K1 region. In another preferred group of HGF variants a functional Kringle 2 (K2) region is additionally present. We have found that huHGF variants composed of the finger and K1 and/or K2 domains of native huHGF retain the ability to bind heparin, i.e. contain at least one heparin-binding site. Single-chain HGF variants, which are resistant to proteolytic cleavage by trypsin-like proteases at the one-chain to two-chain cleavage site between Arg494 and Val495 of native huHGF are able to bind the HGF receptor but substantially lack biological activity (i.e. they are HGF inhibitors). Such variants preferably contain single or multiple amino acid substitutions, insertions and/or deletions at or adjacent to amino acid positions 493, 494, 495 and 496 of the native huHGF amino acid sequence. A preferred alteration is the replacement of arginine at amino acid position 494 with any other amino acid, preferably glutamic acid, aspartic acid or alanine. Alterations that potentially increase the receptor binding capacity of native huHGF are, for example, in the amino acid region corresponding to a potential serine protease active site. This region includes amino acids Q534, Y673 and V692 in the native huHGF amino acid sequence. The replacement of these amino acids with any other amino acid, and preferably with amino acids of different size and/or polarity is believed to further improve the receptor binding properties of huHGF.

In another preferred embodiment, the heparin-binding protein is a selectin or a functional derivative thereof. The selectin preferably is L-selectin (U.S. Pat. No. 5,098,833 issued 24 Mar. 1992) or E-selectin. Functional derivatives of selectins are also known and, for example, disclosed in U.S. application Ser. No. 07/879,036 filed 30 Apr. 1992 abandoned. If the functional derivative of a selectin is an amino acid sequence variant, it will ordinarily have a lectin domain, the amino acid sequence of which is substantially homologous (more than about 80% based on complete amino acid identity, ignoring insertions and deletions) to that of a native selectin molecule. The amino acid residues identified as primarily involved with the recognition of the carbohydrate ligands of selectins are a relatively small patch on the surface of the selectin lectin domain near the anti-parallel beta sheet formed by the disulfide-linked N- and C-termini and the adjacent disulfide-linked loop formed by the two internal cysteines. A significant increase in ligand binding has been described for selectin variants having a amino acid substitution at position 8. In particular, the substitution of alanine for glutamic acid (a charged residue) at position 8 of E-selectin, and the mutation of lysine to alanine at this site in L- and P-selectin was found to significantly enhance ligand recognition. The use of selectin variants containing one or more amino acid alterations in the amino acid regions 7–9, 43–48, 82–86, 90–109, and at amino acid positions 111 and 113 is specifically within the scope of the present invention.

The heparin-binding protein and the binding inhibitory compound, which is typically a polyanionic compound, can be incorporated in the same pharmaceutical formulation or may be otherwise coadministered, wherein coadministration includes simultaneous and tandem administrations in either order, provided that the polyanionic compound is administered at a time when no significant amount of the heparin-binding compound has been removed from the blood stream. This time is preferably not later than the time by which about 10% of the original dose administered has been removed from the circulation.

Dosages of the heparin-binding proteins and their functional derivatives administered in accordance with the present invention may vary depending on the actual compounds used, and on the use envisioned. A typical effective dose of HGF in rat experiments is about 250 µg/kg administered as an intravenous bolus injection. Interspecies scaling of dosages can be performed in a manner known in the art, e.g. as disclosed by Mordenti et al., *Pharmaceut. Res.* 8, 1351 (1991). The therapeutically effective daily dose of native huHGF typically is about 0.01 to 100 mg in human patients, which can be administered as a single dose or in the form of multiple doses. Typical doses and formulations of L-selectin are, for example, disclosed in U.S. Pat. No. 5,098,833 issued 24 Mar. 1992.

In general, suitable ingredients for use in pharmaceutical compositions are described in *Remington's Pharmaceutical Sciences*, 16th edition, 1980, Mack Publishing Co., edited by Oslo et al.

The ratio of the heparin-binding protein and the polyanionic compound, such as heparin or heparin-derived oligosaccharides, is believed to be not critical. As a general proposal, the polyanionic compound is used in molar excess as compared to the heparin-binding protein. For HGF, this can be an about 10-fold mass excess. The determination of the optimum ratio for each combination of heparin-binding proteins and polyanionic compounds is well within the skill in the art. The actual dose of the polyanionic compound used in association with a heparin-binding protein also depends on the purpose of administration. For example, as shown in Example 6, the bioavailability of HGF is efficiently increased by dextran sulfate administered in a 1:1–1:10, preferably 1:1–1:2 HGF/dextran sulfate molar ratio, preferably using an about 2 to 5 mg/kg/day dose of dextran sulfate. Similar ratios and total doses for other heparin-binding protein/polyanionic compound pairs can be determined experimentally.

The polyanionic compounds used in accordance with the present invention can be incorporated into pharmaceutical compositions known for the administration of the corresponding heparin-binding proteins.

The coadministration in accordance with the present invention specifically includes the possibility of administering more than one heparin-binding protein and more than one polyanionic compound, as it might be desirable for any given application.

Further details of the invention are illustrated in the following non-limiting examples.

EXAMPLE 1 (FIG. 1)

The effect of heparin on the biological activity of HGF

The effect of heparin on the biological activity of single chain HGF was measured by comparing the ability of HGF alone or in the presence of heparin to induce DNA synthesis in rat hepatocytes in primary culture (Lokker et al., *EMBO J.* 11: 2503–2510 (1992)). Hepatocytes were isolated according to published perfusion techniques (Garrison and Haynes, *J. Biochem.* 250, 2269–2777 (1975)) and resuspended at $1 \times 10^5$ cells/ml in serum-free bioassay medium containing Williams media, insulin, transferrin, glutamine, BSA and antibiotics. Hepatocytes were then incubated in 96-well plates in the presence of duplicate serial dilutions of rhuHGF. To some wells, heparin was added at 0.1, 1.0, or 10 µg/mL. After 48 hr incubation at 37° C., 0.5 mCi[$^3$H]TdR (15 Ci/mmol, Amersham) was added to each well and incubated for an additional 16 hr. Cells were harvested on filter papers, which were washed, dried and counted in a Beckman counter after addition of scintillation fluid. Relative radioactivity incorporated into hepatocytes is plotted as a function of HGF concentration.

EXAMPLE 2 (FIG. 2)

The effect of heparin on the detection of HGF in an ELISA

Either single chain (panel a) or two chain (panel B) HGF concentrations were measured using a buffer-based immunoassay in the presence of varying concentrations of heparin (0, 0.1, and 10 µg/ml). HGF and heparin were diluted in ELISA diluent containing PBS, 0.1% BSA, and 0.05% Tween-20. The ELISA assay used monoclonal antibody A.3.1.2 as a coat antibody and B.4.3 conjugated to horse radish peroxidase for detection.

EXAMPLE 3 (FIGS. 3A–3B)

The effect of heparin on the pharmacokinetics of HGF in vivo

New Zealand white rabbits (n=3/group) were injected with an iv bolus dose of HGF (0.2 mg/kg) in the presence and absence of 200 units heparin/kg. Blood samples were harvested at various times following injection. HGF concentrations in rabbit plasma were measured using a plasma-based HGF specific ELISA. The weight normalized clearance, CL, initial volume of distribution, $V_1$, steady state volume of distribution, Vss, mean residence time, MRT, and half-life, $t_{1/2}$ are presented.

EXAMPLE 4 (FIG. 4).

The effect of polyanions on the bioavailability of HGF after subcutaneous administration Rats (n=6/group) received subcutaneous injections of HGF (500 µg/kg) in the presence or absence of a 10-fold mass excess of various polyanions. HGF was allowed to incubate with the respective polyanion for 60 min at room temperature prior to injection. Rat blood samples were removed 60 min following HGF administration. HGF concentrations in blood were monitored using a plasma based ELISA.

EXAMPLE 5 (FIGS. 5A–5B)

The effect of heparin on the hepatic clearance of [$^{125}$I]HGF

The effect of heparin on the hepatic clearance of HGF was studied in a single pass liver perfusion (SPLP) experiment. Approximately 10 ng/ml [$^{125}$I]HGF was infused via the portal vein into a rat liver in the presence or absence of heparin. The amount of HGF that was not bound by the liver after a single pass was determined and expressed as percent of infused dose. Both total and TCA precipitable radioactivity were monitored.

EXAMPLE 6

Increase of bioavailability of HGF/SF by coadministration of dextran sulfate

MATERIALS AND METHODS

Animals: Male C3H/HeJ mice were obtained from The Jackson Laboratory (Bar Harbor, Me.) at 6–8 weeks of age (body weight=23–27 g) and allowed to acclimatize for at least one week before use. Food (Formulab Chow, Purina Miles, Inc.) and water were provided ad libitum, room temperature was maintained at 72° F., and the light:dark cycle as 12h:12h. All experiments were approved and monitored by the Genentech Animal Care and Use Committee, following guidelines established by the National Institutes of Health.

Recombinant human HGF/SF was produced at Genentech, Inc. (South San Francisco, Calif.) and formulated in 20 mM TrisHCl (pH 7.5), 500 mM NaCl. Endotoxin levels were <2 EU/mg, as determined in the limulus lysate assay. Dextran sulfate (sodium salt, average MW=5,000) was purchased from Sigma Chemical Co. (St. Louis, Mo.). HGF/SF and/or dextran sulfate were diluted with 0.9% pyrogen-free saline (McGaw, Inc., Irvine, Calif.), sterilized using 0.2 mm filters (Millipore Products Division, Bedford, Mass.), and then loaded under sterile conditions into Alzet Model 1003D osmotic minipumps (Alza Corporation, Palo Alto, Calif.), which have a nominal delivery rate of 24 ml/day. In some experiments in which the HGF/SF concentration in the pump load was less than 1 mg/ml, bovine serum albumin (Sigma Chemical Co., St. Louis, Mo.) was included at 1 mg/ml. Pumps were implanted intraperitoneally through a midline incision, using aseptic technique. Anesthesia was induced with ketamine (Ketaset, Aveco Co., Iowa City, Iowa, 75 mg/kg) and xylazine (Rompin, Rugby Laboratories, Inc., N.Y., 7.5 mg/kg). The animals were allowed to recover on heating pads and returned to group caging. Pumps were always implanted in the late afternoon and experiments were terminated in the morning three days (~66 hours) later so that the pumps were allowed to deliver HGF/SF as long as possible, but samples were collected before the pumps were exhausted.

Analyses: Body weight was recorded, then trunk blood was collected by cardiac puncture under ketamine-xylazine anesthesia. One aliquot was added to an EDTA microtainer tube and the remainder was allowed to clot. Serum and plasma samples were stored at −70° C. Wet weights of liver, kidneys, and spleen were recorded.

For histological analysis, portions of tissue were fixed in 10% neutral buffered formalin and paraffin sections were stained with hematoxylin and eosin. Mitotic figures were scored in 20 fields under 20× objective. Fields were selected blindly and those in which hepatic parenchyma did not occupy the entire field—for example, fields that contained large veins or were transected by the edge of the section—were excluded. The analysis was performed by an individual blinded to the treatment groups.

DNA was quantitated after extraction and precipitation with trichloroacetic acid (Burton, K. A., *Biochem. J.* 62, 315–323 [1956]). Plasma concentrations of recombinant human HGF were measured using a specific sandwich ELISA, as described previously (Mendenhall et al., *Hepatol.* submitted, 1994). Serum biochemistries were measured on a Monarch Model 2000 Model 761 Microcentrifugal Chemistry Analyzer (Instrumentation Laboratories, Lexington, Mass.).

Statistical Methods: Animals were randomly assigned to treatment groups and all experiments were performed in a blinded manner. The results are expressed as mean ±SEM of 5–8 animals. Data were analyzed by analysis of variance, followed by Duncan's multiple range test, except that histological scoring was analyzed nonparametrically, using the Mann-Whitney U test.

RESULTS

HGF/SF was loaded into osmotic minipumps alone or in combination with dextran sulfate. We had previously found that bioavailability of HGF/SF after subcutaneous or intraperitoneal injection was markedly enhanced when HGF/SF was premixed with dextran sulfate. In those studies, a 10-fold mass excess of dextran sulfate was used. In Experiment 1, the concentration of HGF/SF in the pumps was 2.4 mg/ml, which produced a daily dose of 2.4 mg/kg, and the HGF/SF:dextran sulfate ratio was 1:10, as used in the injection studies. We also tested a 1:2 ratio. The pumps were implanted in the late afternoon and the animals were killed in the morning 3 days later (~66 hours). As shown in the upper portion of Table 1, plasma levels of immunoactive HGF/SF in Experiment 1 were increased slightly but significantly when HGF/SF alone was infused, compared to vehicle-treated controls, but there was no effect on wet liver weight. Dextran sulfate alone also had no effect. When HGF/SF was combined with a 2-fold mass ratio of dextran sulfate, plasma HGF levels were increased further than with HGF alone. Moreover, there was a significant increase in liver wet weight. There was no effect on serum HGF or liver wet weight when the HGF/SF:dextran sulfate ratio was 1:10.

At the concentrations of dextran sulfate needed to achieve the 1:10 ratio, the material was extremely viscous. Therefore, in Experiment 2, we tried HGF/SF:dextran sulfate ratios of 1:2 and 1:1, with the daily HGF/SF dose again fixed at 2.4 mg/kg. As shown in the lower portion of Table 1, this experiment confirmed the increases in serum HGF/SF levels and liver weight after infusion of HGF/SF with dextran sulfate at a 1:2 mass ratio. Similar effects were observed at a 1:1 ratio and this ratio was used in all subsequent experiments.

Figure 6:
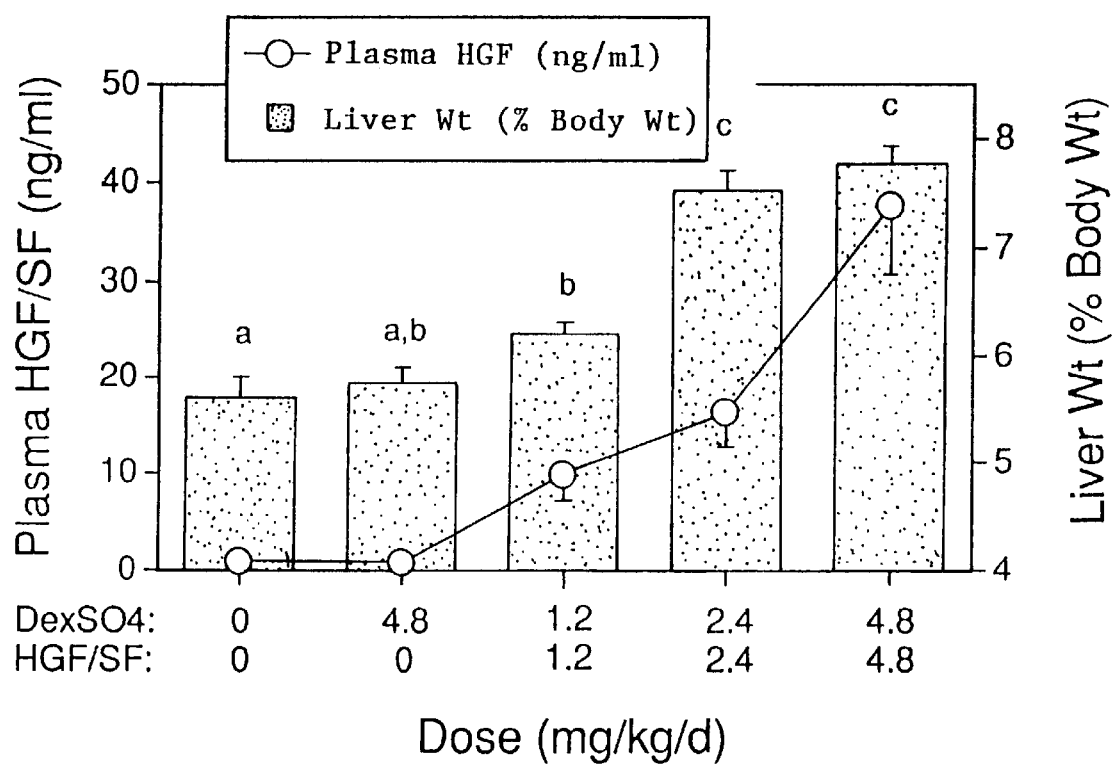
FIG. 6 shows HGF/SF dose-response. Osmotic minipumps loaded to deliver the indicated doses of HGF/SF and/or dextran sulfate were implanted in the peritoneal cavity of adult mice. Three days later, plasma HGF/SF and liver weight were determined. Bars and symbols represent means ±SEM for 6 animals. Bars identified by different letters are significantly different (P<0.05).
Figure 7:
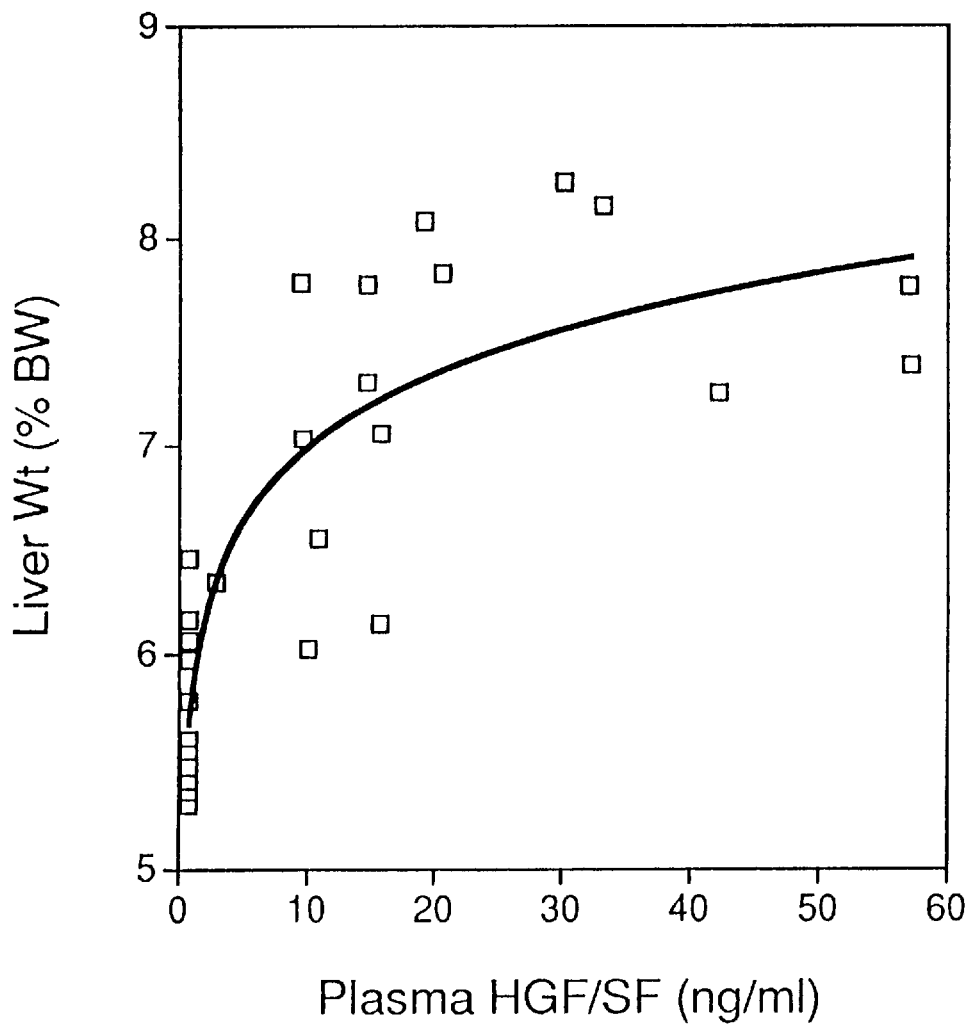
FIG. 7 shows saturability of HGF/SF-induced liver growth. Liver weight was plotted as a function of plasma HGF/SF for individual mice that were infused intraperitoneally for 3 days with saline, dextran sulfate alone at 4.8 mg/kg/d, or HGF/SF plus dextran sulfate at doses of 1.2, 2.4, or 4.8 mg/kg/d.

In Experiment 3, we tested several different doses of HGF/SF (0.27, 0.8 or 2.4 mg/kg/d), with the HGF/SF:dextran sulfate ratio held constant at 1:1. Consistent with earlier experiments, liver weight was increased in the 2.4 mg/kg/d group (6.9±0.1% body Wt for HGF/SF-treated animals, vs 5.5±0.2 for controls, P<0.01), but there was no effect at the two lower HGF/SF doses (data not shown). In Experiment 4, HGF/SF doses of 1.2, 2.4, and 4.8 mg/kg/d were tested, again with a fixed 1:1 HGF/SF:dextran sulfate ratio. One control group received pumps containing only the buffer vehicle. A second control group received dextran sulfate alone at 4.8 mg/kg/d. There were no controls treated with lower doses of dextran sulfate alone. As shown in FIG. 6, serum HGF/SF levels were very low in controls that received neither HGF/SF nor dextran sulfate, and in animals given dextran sulfate alone, but were increased in a dose-dependent manner when the pumps contained increasing concentrations of HGF/SF. Liver weight was increased markedly in both the 2.4 and 4.8 mg/kg/d dose groups compared to controls, and these two groups were not different from each other. When liver wet weight was plotted against plasma HGF/SF in individual animals, liver wet weight increased as plasma HGF/SF levels rose above baseline but reached a plateau (FIG. 7).

We repeated these studies several times and as can be seen in Table 2, enlargement of the liver, measured either as absolute liver weight or normalized to body weight, was observed in every experiment in which the HGF/SF dose was 2.4 mg/kg/d or greater. The average increase in size was 27±8%. In contrast, there was no effect on the weight of kidney or spleen in any experiment (Table 2).

Figure 8A:
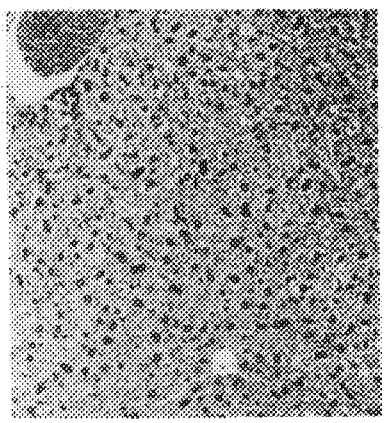
FIGS. 8A–8C shows histology. Representative histological sections of liver from control animals (A) and from animals treated with HGF/SF plus dextran sulfate (B and C). Heavy arrows identify cells in metaphase, script arrows show cells in telophase.
Figure 8B:
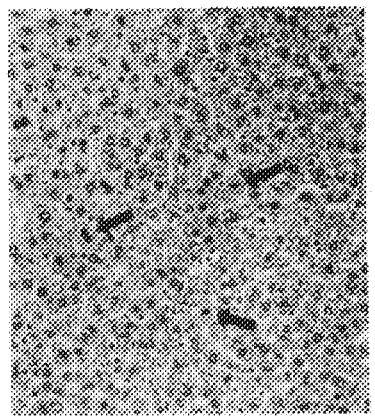
Figure 8C:
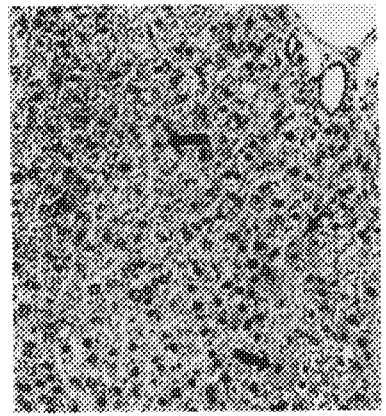

On gross examination, livers from control and HGF/SF treated animals differed only in size. Histologically, the livers induced to grow by HGF/SF-dextran sulfate looked normal, except that mitotic figures, which were rarely found in sections of control liver, were frequently seen in HGF/SF-treated animals (FIGS. 8A–8C). To quantify this effect, the number of mitotic figures in 20 randomly-selected fields were counted. The results are shown in Table 3. An average of ~1 mitotic figure was found throughout all 20 fields from control livers and from livers exposed to either dextran sulfate alone or 1.2 mg/kg/d HGF/SF. In contrast, approximately 30 figures were found in the 20 fields from livers exposed to higher doses of HGF/SF, or 1–2 in each field. No mitotic figures were observed in bile duct epithelium. Total liver DNA increased by 21% in Experiment 5 and by 34% in Experiment 6 (Table 3), although this effect did not reach statistical significance in Experiment 5 (P=0.14).

Serum samples from HGF/SF-treated animals were frequently lipemic, which led us to measure a panel of serum biochemistries (Table 4). Consistent with the lipemic appearance, serum triglycerides and cholesterol were markedly elevated in a dose-dependent manner. In addition, total serum protein and serum albumin were increased. Conversely, alkaline phosphatase was reduced by HGF/SF. No effect on either ALT (Table 4) or AST (not shown) was detected in any experiment.

DISCUSSION

In the course of studying the effects of HGF/SF in animal models, we found that HGF/SF is very poorly absorbed into the blood stream after subcutaneous injection. Bioavailability was better after intraperitoneal injection, but still poor. Consistent with these observations, studies that have shown activities of HGF/SF in vivo have used intravenous delivery (Fujiwara et al., *Hepatol.* 18, 1443–1449 [1993]; Ishiki et al., *Hepatol.* 16, 1227–1235 [1992]; Roos et al., *Endocrinol.* 131, 2540–2544 [1992]). Because HGF/SF is cleared very rapidly (Appasamy et al., *Lab. Invest.* 68, 270–276 [1993];

Zionchem. et al., *Endocrin.* 134, 1879–1887 [1994]), serum levels are elevated for only brief periods of time following each iv injection. The data presented here show that intraperitoneal infusion of HGF/SF combined with dextran sulfate provides sustained elevations in circulating HGF/SF levels.

The absolute values for plasma HGF/SF varied among experiments. As an extreme example, the same dose of HGF/SF and dextran sulfate (2.4 mg/kg/d and 4.8 mg/kg/d, respectively) produced plasma levels of 28.3 ng/ml in Experiment 1 and 7.1 ng/ml in Experiment 2 (see Table 1). The source of this variability is unclear but seems to be related more to inter-experiment factors than interassay variability because similar values were obtained when representative samples were re-run within a single ELISA. It is for this reason that the correlation between plasma HGF/SF and liver weight shown in FIG. 7 was limited to data from a single experiment.

The rationale for the use of dextran sulfate is that in a separate series of experiments, we found that premixing of HGF/SF with soluble heparin greatly enhanced its bioavailability from subcutaneous and intraperitoneal sites (unpublished observation). This effect was not specific to heparin and was also observed with other sulfated polysaccharides including pentosan polysulfate, hyaluronate, and dextran sulfate. Dextran sulfate was chosen arbitrarily for the infusion studies. At a 1:10 HGF/SF:dextran sulfate ratio the solution was extremely viscous and probably could not get out of the infusion pump. However, ratios of 1:1 or 1:2 enhanced the effectiveness of HGF/SF infusions. Although not fully understood, it is believed that because HGF/SF binds heparin strongly (Nakamura et al., *Proc. Natl. Acad. Sci. USA* 83, 6489–6493 [1986]), its absorption from subcutaneous and intraperitoneal sites is low due to trapping by interaction with heparin sulfate proteoglycans in the extracellular matrix. It is believed that sulfated polysaccharides may saturate the heparin binding regions on HGF/SF, thereby preventing interaction with matrix components. Heparin also decreases the clearance of HGF/SF, and sulfated polysaccharides enhance hepatocyte responses to low doses of HGF/SF.

Using this delivery system, we have been able to induce growth of liver in an otherwise intact animal. While this work was in progress, Fujiwara et al. reported that HGF stimulated liver growth in normal rats and enhanced the amount of liver regenerated after partial hepatectomy (Fujiwara et al., *Hepatol.* 18, 1443–1449 [1993]). In those studies, HGF was injected intravenously every 2 hours for 10 hours. Each injection was 10 µg/100 g body weight, a total dose 500 µg/kg. This dose is lower than the daily dose we found to be necessary to induce comparable liver growth in our studies, but it compares favorably when one considers that in our studies the material was delivered by continuous extravascular infusion while in those of Fujiwara et al., it was delivered directly into the bloodstream. To our knowledge, these are the only two reports that a growth factor has been able to induce growth of normal liver in vivo, despite the fact that a large number of proteins can stimulate hepatocyte DNA synthesis in vitro.

A major mechanism for the HGF/SF-induced increase in wet liver weight appears to be stimulation of hepatocyte proliferation. Mitotic figures, which are rarely observed in histological sections from control liver, were abundant in livers exposed to HGF/SF. Mitoses were found randomly distributed throughout the hepatic lobule, with no apparent association with vascular elements. Although HGF/SF has been reported to stimulate DNA synthesis in nonparenchymal cells and bile duct epithelial cells in vitro (Joplin et al., *J. Clin. Invest.* 90, 1284–1289 [1992]), we observed no mitotic figures in bile duct epithelial cells. However, the number of such cells in any section is very small compared to the number of hepatocytes, so a modest amount of proliferation in this compartment would be difficult to detect histologically.

Hepatic DNA content was elevated in the HGF/SF-treated animals in both experiments in which it was measured, although this did not reach statistical significance in Experiment 5. The difference in DNA levels between these two experiments are due to fact that polypropylene tubes were used for the DNA assay in Experiment 5 while glass tubes were used for Experiment 6; dissolution of the pellet after TCA precipitation was easier in glass tubes, giving better extraction efficiency.

There also appears to be a component of the increase in liver wet weight that is not related to proliferation. For example, a dose of 1.2 mg/kg/d clearly had no effect on mitotic activity (Table 3), but caused significant increases in liver wet weight (Table 3), serum lipids (Table 4), and a significant decrease in alkaline phosphatase (Table 4). Others have reported striking effects of HGF/SF on the morphology of several cell types (Bhargava et al., *EXS* 65, 341–349 [1993]; Li et al., *In Vitro. Cell Dev. Biol.* 28A, 364–368 [1992]; Uehara et al., *J. Cell. Biol.* 117, 889–894 [1992]), suggesting that it may have trophic as well as proliferative actions in target tissues. Our data are consistent with such a trophic action in the liver.

Expression of HGF/SF in the kidney has been shown to increase following unilateral nephrectomy, which has raised the suggestion that HGF/SF is important in compensatory renal hypertrophy (Nagaike et al., *J. Biol. Chem.* 266, 22781–22784 [1991]). However, we consistently found no effect on kidney size, despite the fact that liver size was increased in every experiment. Infusions of longer duration have also shown no effects on kidney size (unpublished observation). The sensitivity of the kidney to HGF/SF may be regulated locally in different physiological states.

Lastly, we observed that HGF/SF-induced liver growth was associated with changes in serum biochemistry, the most striking of which was lipemia. Total protein and serum albumin were also markedly elevated. The reason that alkaline phosphatase was reduced is unknown. Nonetheless, these results indicate that HGF/SF has major effects on hepatic function, as well as size.

In addition, we have shown that normal liver can be induced to grow by treatment with intraperitoneally administered HGF/SF in the absence of any other perturbation or stimulation. The increase in liver size was accompanied by marked increases in proliferative activity of hepatocytes and in increases in the level of serum protein and lipid.

In conclusion, we have shown that intraperitoneal infusion of HGF/SF in combination with dextran sulfate is an effective mechanism for providing sustained elevations in circulating HGF/SF.

TABLE 1

Effect of Infusion of HGF/SP with Dextran Sulfate on Plasma HGF and Liver Weight.

| Experiment | Dose (mg/kg/d) HGF/SF | Dose (mg/kg/d) DexSO$_4$ | Ratio | Plasma HGF/SF (ng/ml) | Liver Weight (% Body Wt) |
|---|---|---|---|---|---|
| 1 | 0 | 0 |  | 0.9 ± 0.4 | 5.8 ± 0.1 |
|  | 2.4 | 0 | 0 | 5.9 ± 2.0* | 5.7 ± 0.2 |
|  | 0 | 4.8 |  | 0.5 ± 0.1 | 5.9 ± 0.2 |
|  | 2.4 | 4.8 | 1:2 | 28.3 ± 10.7 | 7.1 ± 0.5* |
|  | 0 | 24.0 |  | 0.6 ± 0.2 | 5.5 ± 0.1 |
|  | 2.4 | 24.0 | 1:10 | 1.1 ± 0.5 | 5.5 ± 0.1 |
| 2 | 0 | 0 | 0 | 0.6 ± 0.1 | 5.4 ± 0.1 |
|  | 0 | 4.8 |  | 0.6 ± 0.1 | 5.8 ± 0.2 |
|  | 2.4 | 4.8 | 1:2 | 7.1 ± 1.8* | 6.4 ± 0.2* |
|  | 0 | 2.4 |  | 0.5 ± 0.1 | 5.4 ± 0.2 |
|  | 2.4 | 2.4 | 1:1 | 6.0 ± 2.3* | 6.2 ± 0.1* |

Osmotic minipumps filied to deliver the indicated doses of HGF/SF and dextran sulfate were implanted intraperitoneally in intact mice. Plasma: HGF and liver wet weight were determined on the third day of infusion. Values are means ± SEM, n = 5–6 per group.
*Different from untreated control group in the same experiment (P < 0.01).

TABLE 2

Effects of 3-day infusions of HGF/SF and dextran sulfate on wet weights of liver, kidney, and spleen.

| Exp No. | Dose (mg/kg/d) HGF/SF | Dose (mg/kg/d) DexSO4 | Liver Weight Absolute (g) | Liver Weight (% Body Wt) | % Increase | Kidney Wt (Pair) (% Body Wt) | Spleen Wt (% Body Wt) |
|---|---|---|---|---|---|---|---|
| 2 | 0 | 2.4 | 1.22 ± 0.04 | 5.4 ± 0.2 |  | 1.60 ± 0.07 | 0.44 ± 0.01 |
|  | 2.4 | 2.4 | 1.42 ± 0.03* | 6.2 ± 0.1* | 15% | 1.60 ± 0.11 | 0.41 ± 0.03 |
| 3 | 0 | 2.4 | 1.30 ± 0.05 | 5.7 ± 0.1 |  | 1.10 ± 0.05 | 0.41 ± 0.02 |
|  | 2.4 | 2.4 | 1.54 ± 0.03* | 6.9 ± 0.1* | 21% | 1.68 ± 0.03 | 0.40 ± 0.02 |
| 4 | 0 | 4.8 | 1.29 ± 0.05 | 5.1 ± 0.2 |  | 1.62 ± 0.03 | 0.38 ± 0.01 |
|  | 2.4 | 2.4 | 1.69 ± 0.07* | 7.5 ± 0.2* | 32% | 1.63 ± 0.03 | 0.42 ± 0.02 |
|  | 4.8 | 4.8 | 1.63 ± 0.02* | 7.8 ± 0.2* | 37% | 1.59 ± 0.01 | 0.41 ± 0.01 |
| 5 | 0 | 4.8 | 1.11 ± 0.03 | 5.4 ± 0.1 |  | ND | ND |
|  | 4.8 | 4.8 | 1.45 ± 0.06* | 7.2 ± 0.2* | 33% | ND | ND |
| 6 | 0 | 2.4 | 1.47 ± 0.05 | 5.9 ± 0.1 |  | 1.77 ± 0.02 | 0.35 ± 0.02 |
|  | 2.4 | 2.4 | 1.85 ± 0.07* | 7.4 ± 0.3* | 25% | 1.82 ± 0.03 | 0.36 ± 0.02 |
| Overall |  |  |  |  | 27 ± 8 |  |  |

Adult mice were infused intraperitoneally with the indicated doses of HGF/SF and dextran sulfate. Three days later organ weights were determined. Values are means ± SEM, n = 5–7 per group. ND = Not Determined.
*P < 0.01 compared to dextran sulfate alone within the same experiment.

TABLE 3

Mitotic activity and DNA content liver after infusion of HGF/SF.

| Exp No. | Dose (mg/kg/d) HGF/SF | Dose (mg/kg/d) DexSO$_4$ | Liver Wt (% Body Wt) | Mitoses per 20 fields | Liver DNA (mg/100 g BW) |
|---|---|---|---|---|---|
| 4 | 0 | 0 | 5.6 ± 0.2 | 0.8 ± 0.5 | ND |
|  | 0 | 4.8 | 5.7 ± 0.2 | 0.3 ± 0.2 | ND |
|  | 1.2 | 1.2 | 6.2 ± 0.1* | 0.8 ± 0.4 | ND |
|  | 2.4 | 2.4 | 7.5 ± 0.2** | 37.0 ± 19.6** | ND |
|  | 4.8 | 4.8 | 7.8 ± 0.2** | 54.0 ± 6.9** | ND |
| 5 | 0 | 4.8 | 5.4 ± 0.1 | 1.5 ± 0.8 | 10.7 ± 0.6 |
|  | 4.8 | 4.8 | 7.2 ± 0.2 | 29.8 ± 9.8** | 12.9 ± 1.2 |
| 6 | 0 | 2.4 | 5.9 ± 0.1 | 0.8 ± 0.5 | 13.7 ± 0.7 |
|  | 2.4 | 2.4 | 7.4 ± 0.3** | 30.3 ± 14.9** | 18.3 ± 1.1** |

Adult mice were infused intraperitoneally with the indicated doses of HGF/SF and dextran sulfate for three days. A portion of liver was then fixed and sections were stained with hematoxylin and eosin. The number of mitotic figures in 20 fields under a 20× objective was counted in a blinded manner. DNA was extracted for an additional portion of liver. Values are means ± SEM, n = 5–7 per group. ND = Not Determined.
*P < 0.05, **P < 0.01 compared to control group within the same experiment.

TABLE 4

Effects of 3-day infusions of HGF/SF and dextran sulfate on serum biochemistry.

| Exp. No. | Dose (mg/kg/d) HGF/SF | Dose (mg/kg/d) DexSO4 | Liver wt (% Body WT) | Triglycerides (mg/dl) | Cholesterol (mg/dl) | Total Protein (g/dl) | Albumin (g/dl) | Alk. Phos. (U/L) | ALT (IU/L) |
|---|---|---|---|---|---|---|---|---|---|
| 3 | 0 | 0 | 5.7 ± 0.1 | 104 ± 9 | ND | ND | ND | 85 ± 2 | 50.2 ± 15.7 |
|   | 0 | 2.4 | 5.7 ± 0.1 | 129 ± 10 | ND | ND | ND | 77 ± 4 | 78.4 ± 19.6 |
|   | 2.4 | 2.4 | 6.9 ± 0.1 | 281 ± 63** | ND | ND | ND | 52 ± 3** | 55.5 ± 18.6 |
| 4 | 0 | 0 | 5.6 ± 0.2 | 134 ± 29 | 151 ± 7$^a$ | ND | ND | 70 ± 3$^a$ | 45.3 ± 8.3 |
|   | 0. | 4.8 | 5.7 ± 0.2 | 102 ± 23 | 147 ± 5$^b$ | ND | ND | 71 ± 1$^a$ | 37.2 ± 5.6 |
|   | 1.2 | 1.2 | 6.2 ± 0.1* | 155 ± 18 | 224 ± 3$^b$ | ND | ND | 54 ± 3$^b$ | 45.8 ± 9.0 |
|   | 2.4 | 2.4 | 7.5 ± 0.2** | 344 ± 81* | 310 ± 16$^c$ | ND | ND | 48 ± 3$^c$ | 37.0 ± 4.8 |
|   | 4.8 | 4.8 | 7.8 ± 0.2** | 751 ± 92** | 406 ± 16$^d$ | ND | ND | 29 ± 9$^d$ | 48.0 ± 10.7 |
| 5 | 0 | 4.8 | 5.4 ± 0.1 | 79 ± 9 | 133 ± 3 | 4.9 ± 0.1 | 3.0 ± 0.1 | 107 ± 7 | 55.0 ± 7.5 |
|   | 4.8 | 4.8 | 7.2 ± 0.2** | 350 ± 82** | 275 ± 30** | 7.3 ± 0.5** | 3.8 ± 0.3* | 72 ± 9** | 48.0 ± 11.7 |
| 6 | 0 | 2.4 | 5.9 ± 0.1 | 113 ± 20 | 110 ± 4 | 4.5 ± 0.1 | 2.7 ± 0.1 | 75 ± 3 | 68.2 ± 20.7 |
|   | 2.4 | 2.4 | 7.4 ± 0.3* | 271 ± 102 | 208 ± 22** | 5.9 ± 0.3** | 3.5 ± 0.1** | 48 ± 4** | 78.0 ± 32.6 |

Adult mice were infused intraperitoneally with the indicated doses of HGF/SF and dextran sulfate for three days, then serum biochemistries were measured. Values are means ± SEM, n = 5–7 per group. ND = Not Determined.
*P < 0.05, **P < 0.01 compared to control group within the same experiment. In Experiment 4, groups marked with different letters are different from each other at P < 0.01. The large error in the HGF/SF group in Experiment 6 was due primarily to one animal with a value of 759 mg/dl.

EXAMPLE 7 (FIGS. 9–11)

The effect of heparin on the biological activity of HGF/NK1

A. Hepatocyte proliferation assay

The effect of heparin on the biological activity of HGF/NK1 was measured by comparing the ability of HGF/NK1, with and without rhuHGF, to induce DNA synthesis in rat hepatocytes cultured in either control medium or medium containing heparin.

The assay was conducted essentially as described in Example 1 above. The hepatocytes were resuspended in the control bioassay medium, medium containing 1–10 μg/ml heparin, or medium containing 10 μg/ml GM-32 (a sulfated tetrasaccharide) and placed in the 96-well culture plates. Designated hepatocyte cultures were then incubated in the presence of rhuHGF (10 ng/ml) or NK1 (10, 100, or 1000 ng/ml) or both rhuHGF and NK1. NK1 was prepared as described by Lokker et al.,*J. Biol. Chem.*, 268:17145–17150 (1993). DNA synthesis was then measured as the relative radioactivity incorporated into the hepatocytes.

Figure 9C:
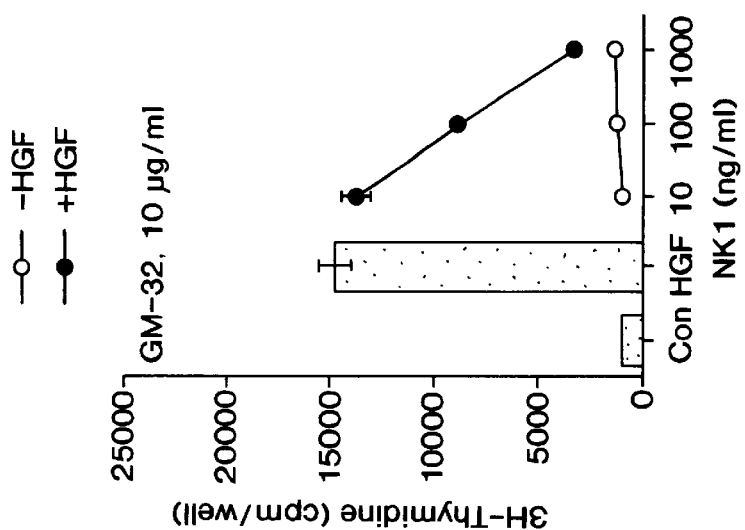
FIGS. 9A–9C shows the effect of heparin on the biological activity of HGF/NK1 in a rat hepatocyte proliferation assay.
Figure 9B:
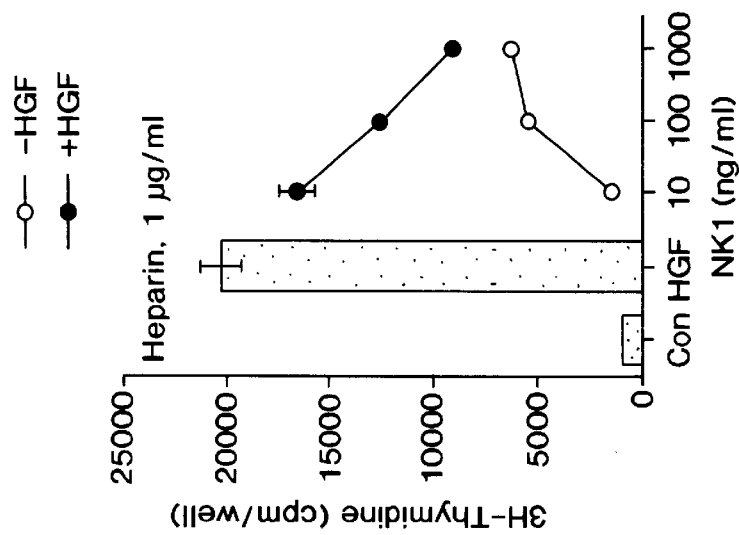
Figure 9A:
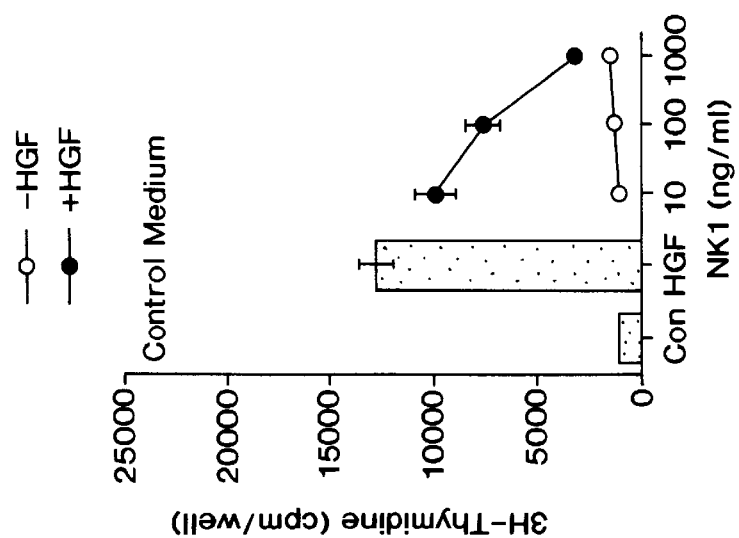

The results are shown in FIGS. 9A–9C. NK1 was a HGF antagonist in the absence of heparin (FIG. 9A), but behaved as a partial agonist when heparin (1 μg/ml) was added to the medium (FIG. 9B). The effect of the heparin was not mimicked by the GM-32 (FIG. 9C). In the hepatocyte cultures, the heparin modulated the activity of the NK1 from a HGF antagonist to a partial agonist or stimulator of hepatocyte growth.

B. BaF3-hMet.8 cell proliferation assay

The effect of heparin on the biological activity of HGF/NK1 was measured by comparing the ability of HGF/NK1, with and without rhuHGF, to induce DNA synthesis and proliferation in BaF3-hMet.8 cells cultured in either control medium or medium containing heparin. BaF3-hmet.8 cells, expressing full length human c-Met, were constructed as follows. An expression plasmid was prepared by inserting a full-length cDNA for human c-Met (described as pOK met cDNA in Rodrigues et al., supra) into a pRK5.tk.neo vector [de Sauvage et al., *Nature*, 369:533–538 (1994); Gorman, *DNA Cloning: A New Approach*, 2:143–190 (IRL Washington 1985)]. The resulting plasmid was linearized and transfected into the IL-3 dependent cell line, BaF3 [Palacios et al., *Cell*, 41:727–734 (1985)] by electroporation (800 microfarad, 250 V, BRL electroporator). The BaF3 cells lack cell surface heparan sulfate proteoglycans. Selection of transfectants was performed by culturing the cells for 2–3 weeks in the presence of 2 mg/ml G418. One of the selected transfectant cell lines, referred to as BaF3-hmet.8, was confirmed by Western blotting to express c-Met. BaF3-hmet.8 also tested positive for response to HGF in a proliferation assay measuring incorporation of $^3$H-thymidine. Neither the parental BaF3 cells nor any cells derived by transfection with the pRK5.tk.neo vector alone were found to express c-Met or respond to HGF in the proliferation assay.

The BaF3-hmet.8 cells were passaged in RPMI medium supplemented with 10% fetal bovine serum, 5% WEHI-conditioned medium (as a source of IL-3) and 2 mM glutamine. Prior to conducting the assay, the cells were washed twice with assay medium (RPMI medium supplemented with 10% fetal bovine serum) and resuspended in assay medium to a concentration of 5×10$^4$ cells/ml. Next, 100 μl of the cells was added to each well in the 96-well culture plates. The BaF3-hmet.8 cells were cultured in the presence of NK1 alone (0.001 μg/ml, 0.01 μg/ml, 0.1 μg/ml, 1.0 μg/ml) or NK1 plus heparin or the control sulfated tetrasaccharide, GM-32. The plates were incubated at 37° C. in 5% CO$_2$ for 15 hours.

One μCi $^3$H-thymidine was added to each well of the culture plates. The cells were harvested 7 hours later and the amount of radioactivity incorporated into the DNA was quantitated (CPM) in a microplate scintillation counter.

Figure 10A:
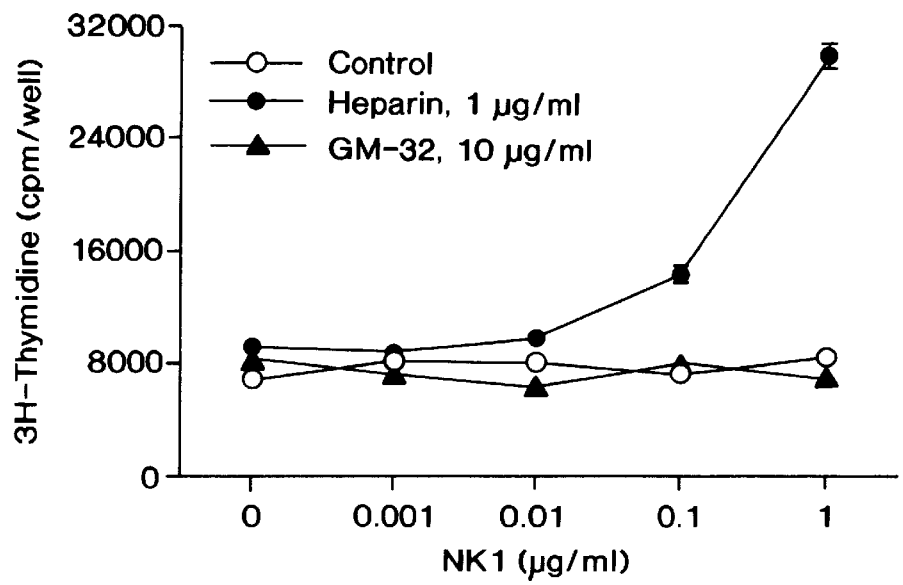
FIGS. 10A–10B show the effect of heparin on the biological activity of HGF/NK1 in an assay measuring DNA synthesis of BaF3-hmet.8 cells.
Figure 10B:
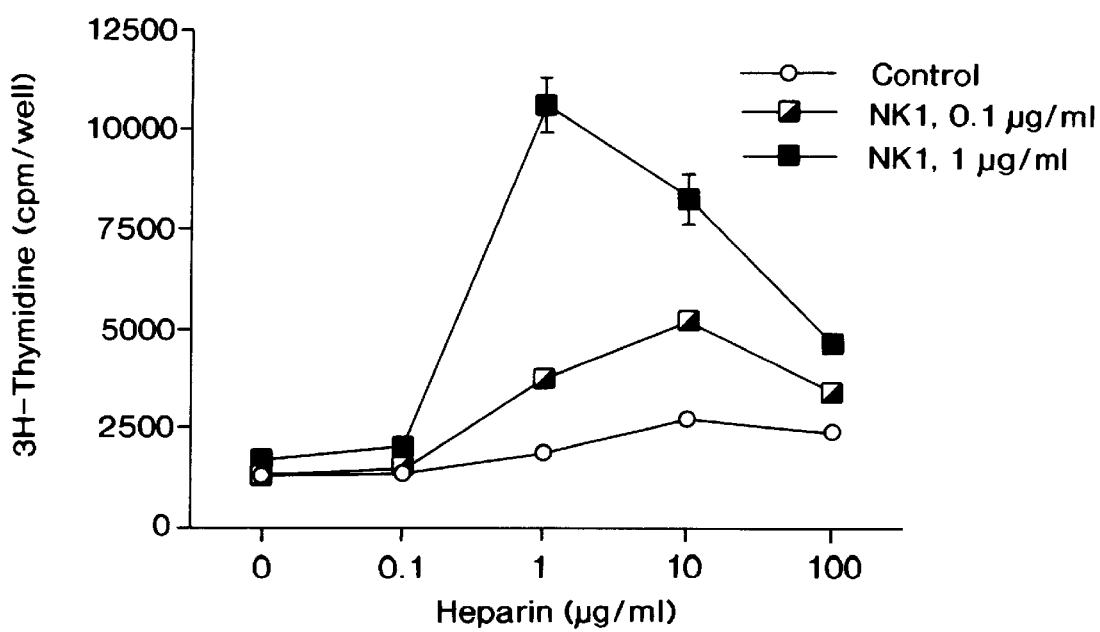

The results are shown in FIGS. 10A–B. As shown in FIG. 10A, NK1 had no effect in the absence of heparin, but stimulated DNA synthesis when heparin was present. GM-32 had no effect. FIG. 10B shows that the effect of heparin was dose-dependent. The heparin dose-response curve was bell-shaped which is consistent with a dimerization mechanism. A direct proliferative effect of NK1 alone was observed in assays of mink lung cells and mammary epithelial cells (data not shown), believed to be due to interactions between NK1 and endogenous cell surface heparan sulfate proteoglycans which are either different or absent in hepatocytes and BaF3-hmet cells. It is believed that the heparin may induce dimerization of NK1, as it does HGF [Zioncheck et al., *J. Biol. Chem.*, in press (1995)].

Figure 11:
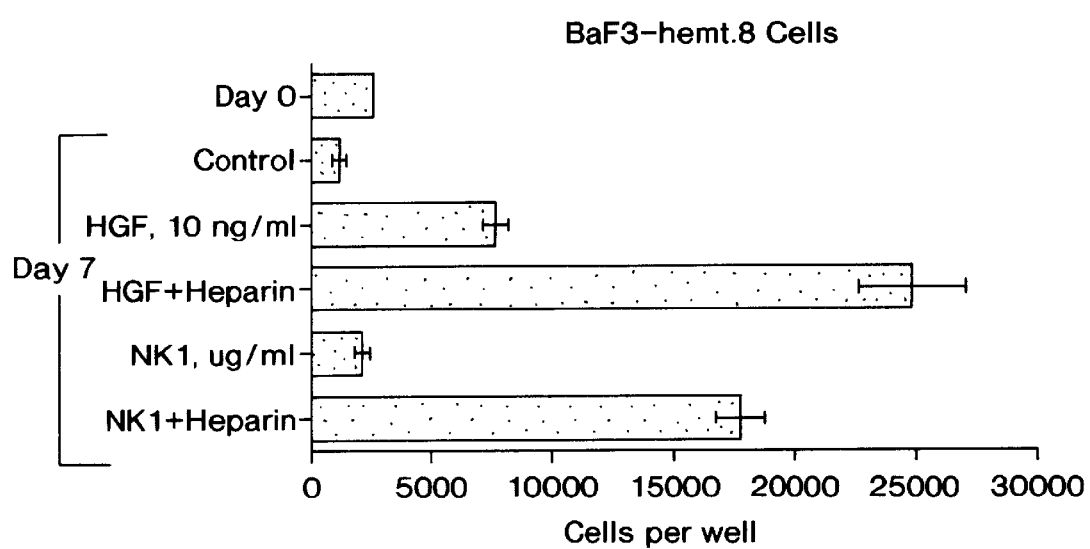
FIG. 11 shows the effect of heparin on the biological activity of HGF/NK1 in a BaF3-hmet.8 cell proliferation assay.

To determine whether the effect of NK1 and heparin on DNA synthesis translated into cellular proliferation, the number of BaF3-hmet.8 cells were counted after 7 days in culture. The medium contained 10% fetal bovine serum but no IL-3. The results are shown in FIG. 11. NK1 alone had no effect but NK1 and heparin stimulated cell growth to nearly the same degree as HGF. The combination of NK1 and heparin was mitogenic, increasing the cell number 15-fold after 7 days. NK1 and heparin had no effect in control BaF3-neo cells, indicating that the response was mediated through c-Met. In both hepatocytes and BaF3-hmet.8 cells, the effective concentration of NK1 (100 ng/ml -1 µg/ml) were consistent with its affinity for c-Met.

The entire disclosures of all citations cited throughout the specification, and the references cited therein, are hereby expressly incorporated by reference.

We claim:

1. A method of extending the plasma half-life of hepatocyte growth factor (HGF)/NK1 comprising coadministering HGF/NK1 with an inhibitor of HGF binding to low affinity heparin-like binding sites.

2. A composition comprising HGF/NK1 in association with a polyanionic compound comprising dextran, dextran sulfate, heparin, or heparin sulfate.

3. A method for inducing hepatocyte growth comprising the intraperitoneal or subcutaneous administration to a patient a composition comprising HGF/NK1 and a polyanionic compound.

4. A method of extending the plasma half-life of a deletion variant of hepatocyte growth factor (HGF) comprising the n-terminal finger and first kringle domain of HGF, the method comprising:
coadministering a therapeutically effective amount of said deletion variant with a composition comprising a polyanionic compound, which polyanionic compound inhibits binding of HGF to low affinity heparin-like binding sites.

5. The method of claim 4 wherein said polyanionic compound is a dextran, a heparin, or a functional derivative thereof.

6. The method of claim 5 wherein said polyanionic compound is heparin sulfate or dextran sulfate.

7. The method of claim 5, wherein said polyanionic compound is a heparin-derived oligosaccharide.

8. The method of claim 4, wherein said polyanionic compound comprises heparin, heparan sulfate, dextran sulfate, pentosan(poly)sulfate, or hyaluronate.

9. The method of claim 4, wherein said deletion variant and said polyanionic compound are administered concurrently.

10. The method of claim 4, wherein said deletion variant and said polyanionic compound are incorporated in the same pharmaceutical composition.

11. The method of claim 4, wherein said deletion variant comprises HGF/NK1 or HGF/NK2.

12. A method for improving the therapeutic potency of a deletion variant of hepatocyte growth factor (HGF) comprising the n-terminal finger and first kringle domain of HGF, the method comprising:
coadministering a therapeutically effective amount of said deletion variant with a composition comprising a polyanionic compound, which polyanionic compound inhibits binding of HGF to low affinity heparin-like binding sites.

13. The method of claim 12, wherein said polyanionic compound is heparin or a functional derivative thereof.

14. The method of claim 12, wherein the polyanionic compound is a heparin-derived oligosaccharide.

15. A method for improving the therapeutic potency of a deletion variant of hepatocyte growth factor (HGF) comprising the n-terminal finger and first kringle domain of HGF, the method comprising:
coadministering a therapeutically effective amount of said deletion variant with heparin, heparin sulfate, heparan sulfate, dextran sulfate, pentosan(poly)sulfate, or hyaluronate.

16. A method of improving the bioavailability of a subcutaneously or intraperitoneally administered deletion variant of hepatocyte growth factor (HGF) comprising the n-terminal finger and first kringle domain of HGF, the method comprising:
coadministering said deletion variant with a compound which inhibits binding of said deletion variant to extracellular matrix.

17. The method of claim 16, wherein said compound is a polyanionic compound.

18. The method of claim 17, wherein said polyanionic compound is a dextran, a heparin, or a functional derivative thereof.

19. The method of claim 18, wherein said polyanionic compound is dextran sulfate.

20. The method of claim 16, wherein said deletion variant comprises HGF/NK1 or HGF/NK2.

21. A method for preventing the inactivation of a deletion variant of hepatocyte growth factor (HGF) comprising the n-terminal finger and first kringle domain of HGF, the method comprising:
coadministering the deletion variant with a polyanionic compound which inhibits binding of said deletion variant to extracellular matrix.

22. The method of claim 21, wherein said polyanionic compound is a dextran, a heparin, or a functional derivative thereof.

23. The method of claim 19, wherein said deletion variant comprises HGF/NK1 or HGF/NK2.

* * * * *